US007659299B2

(12) United States Patent
Pepys et al.

(10) Patent No.: US 7,659,299 B2
(45) Date of Patent: Feb. 9, 2010

(54) COMPOUNDS INHIBITING THE BINDING OF SAP FOR TREATING OSTEOARTHRITIS

(75) Inventors: Mark B. Pepys, London (GB); Philip Nigel Hawkins, London (GB)

(73) Assignee: Pentraxin Therapeutics Limited, London (GB)

( * ) Notice: Subject to any disclaimer, the term of this patent is extended or adjusted under 35 U.S.C. 154(b) by 471 days.

(21) Appl. No.: 10/559,814

(22) PCT Filed: Jun. 10, 2004

(86) PCT No.: PCT/GB2004/002445

§ 371 (c)(1),
(2), (4) Date: Apr. 4, 2006

(87) PCT Pub. No.: WO2004/108131

PCT Pub. Date: Dec. 16, 2004

(65) Prior Publication Data

US 2008/0249003 A1    Oct. 9, 2008

(30) Foreign Application Priority Data

Jun. 10, 2003    (GB) ................................. 0313386.5

(51) Int. Cl.
*A61K 31/40* (2006.01)
*C07D 207/16* (2006.01)
(52) U.S. Cl. .................... 514/408; 548/400; 548/565
(58) Field of Classification Search ..................... None
See application file for complete search history.

(56) References Cited

U.S. PATENT DOCUMENTS

| 4,783,480 A | 11/1988 | Wakatsuka et al. .......... 514/423 |
| 4,895,872 A | 1/1990 | Nitecki et al. ................ 514/546 |
| 6,103,910 A | 8/2000 | Hertel et al. ................. 548/523 |
| 6,126,918 A | 10/2000 | Pepys et al. .................... 424/9.1 |
| 6,365,570 B1 | 4/2002 | Van Kessel et al. ............. 514/8 |
| 7,045,499 B2 | 5/2006 | Pepys ............................ 514/2 |
| 2006/0122124 A1 | 6/2006 | Pepys |

FOREIGN PATENT DOCUMENTS

| EP | 0915088 A1 | 5/1999 |
| WO | WO 95/05394 | 2/1995 |
| WO | WO 97/46098 | 12/1997 |
| WO | WO 98/50420 | 11/1998 |
| WO | WO 03/013508 | 2/2003 |

OTHER PUBLICATIONS

Andersen, O., Vilsgaard Ravn, K.,Sorensen, I.J., Jonson, G., Holm Nielsen, E. and Svehag, S. -E.,Serum amyloid P component binds to influenza A virus haemagglutinin and inhibits the virus infection in vitro. *Scand. J. Immunol.*, 46:331-337, 1997.

Ashton et al., "Pentameric and decameric structures in solution of serum amyloid P component by X-ray and neutron scattering and molecular modelling analyses", *J. Mol. Biol.* 272, 408-422, 1997.

Askarov et al., "Treatment of osteoarthritis deformans with heparin," *Database biosis 'Online! Biosciences information service* 67(3), 190-192, 1986.

Athanasou et al., "Localized deposition of amyloid in articular cartilage," *Histopathology (Oxford)* 20(1) 41-46, 1992.

Baltz et al., "Calcium-dependent aggregation of human serum amyloid P component", *Biochim. Biophys. Acta* 701, 229-236, 1982.

Baltz, M.L., de Beer, F.C., Feinstein, A., Munn, E.A., Milstein, C.P., Fletcher, T.C., March, J.F., Taylor, J., Bruton, C., Clamp, J.R., Davies, A.J.S.and Pepys, M.B. Phylogenetic aspects of C-reactive protein and related proteins. *Ann. N. Y. Acad. Sci.*, 389:49-75, 1982.

Baltz, M.L., Dyck, R.F.and Pepys, M.B., Studies of the in vivo synthesis and catabolism of serum amyloid P component (SAP) in the mouse. *Clin. Exp. Immunol.*, 59:235-242, 1985.

Bartley, C.J., Orford, C.R.and Gardner, D.L., Amyloid in ageing articular cartilage. *J. Pathol.*, 145:107A, 1985.

Booth et al., "Analysis of autoaggregation and ligand binding sites of serum amyloid P component by in vitro mutagenesis", *Amyloid and Amyloidosis 1998*, Ed. By R.A. Kyle and M.A. Gertz, Parthenon Publishing Group, NY, 1998, pp. 23-25.

Booth et al., "Instability, unfolding and aggregation of human lysozyme variants underlying amyloid fibrillogenesis", *Nature* 385, 787-793, 1997.

Borman, "Chemistry Highlights 2002, Medicinal and Combinatorial Chemistry," *Chem. Eng. News* 80, 37-38, 2002.

Breathnach, S.M., Kofler, H., Sepp, N., Ashworth, J., Woodrow, D., Pepys, M.B. and Hintner, H., Serum amyloid P component binds to cell nuclei in vitro and to in vivo deposits of extracellular chromatin in systemic lupus erythematosus. *J. Exp. Med.*, 170:1433-1438, 1989.

Brion, P.H.and Kalunian, K.C.(2003) Osteoarthritis, Oxford Textbook of Medicine, 4th Ed., vol. 3 (Warrell, D.A., Cox, T.M., Firth, J.D.and Benz, E.J., Jr., eds.), Oxford University Press, Oxford, pp. 62-68.

Butler, P.J.G., Tennent, G.A.and Pepys, M.B., Pentraxin-chromatin interactions: serum amyloid P component specifically displaces H1-type histones and solubilizes native long chromatin. *J. Exp. Med.*, 172:13-18, 1990.

Butler, P.J.G., The folding of chromatin. *CRC Crit. Rev. Biochem.*, 15:57-91, 1983.

Cary, N.R.B., "Clinicopathological importance of deposits of amyloid in the femoral head" *J. Clin. Pathol.*, 38:868-872, 1985.

Caspi, D., Zalzman, S., Baratz, M., Teitelbaum, Z., Yaron, M., Pras, M., Baltz, M.L.and Pepys, M.B. "Imaging of experimental amyloidosis with $^{131}$I-serum amyloid P component." *Arthritis Rheum.*, 30:1303-1306, 1987.

Cleaveland et al., "Site of action of two novel pyrimidine biosynthesis inhibitors accurately predicted by the compare program", *Biochem. Pharmacol.* 49(7), 947-954, 1995.

(Continued)

*Primary Examiner*—Ruixiang Li
(74) *Attorney, Agent, or Firm*—Frommer Lawrence & Haug LLP; Thomas J. Kowalski; Deborah L. Lu

(57) ABSTRACT

Use of an agent capable of inhibiting SAP ligand binding activity or depleting SAP from the plasma of a subject for the production of a medicament for treatment or prevention of osteoarthritis in the subject.

6 Claims, 4 Drawing Sheets

OTHER PUBLICATIONS de Beer, F.C., Baltz, M., Holford, S., Feinstein, A.and Pepys, M.B. Fibronectin and C4-binding protein are selectively bound by aggregated amyloid P component. *J. Exp. Med.*, 154:1134-1149, 1981.

de Haas, C.J.C., van Leeuwen, E.M.M., van Bommel, T., Verhoef, J., van Kessel, K.P.M.and van Strijp, J.A.G., Serum amyloid P component bound to gram-negative bacteria prevents lipopolysaccharide-mediated classical pathway complement activation. Infect. Immun., 68:1753-1759, 2000.

Egan, M.S.,Goldenberg, D.L., Cohen, A.S. and Segal, D., The association of amyloid deposits and osteoarthritis. *Arthritis Rheum.*, 25: 204-208, 1982.

Emsley et al., "Structure of pentameric human serum amyloid P component", *Nature 367*, 338-345, 1994.

Goffin, Y.A., Thoua, Y.and Potvliege, P.R., Microdeposition of amyloid in the joints. *Ann. Rheum.Dis.*, 40:27-33, 1981.

Hamazaki et al., Calcium-dependent polymerization of human serum amyloid P component is inhibited by Heparin and dextran sulfate, *Biochimica Et Biophysica Acta 998(3)*, 231-235, 1989.

Hamazaki, H., $Ca^{2+}$-mediated association of human serum amyloid P component with heparan sulfate and dermatan sulfate. *J. Biol. Chem.*, 262:1456-1460, 1987.

Hawkins et al., "Metabolic studies of radioiodinated serum amyloid P component in normal subjects and patients with systemic amyloidosis", *J. Clin. Invest.* 86, 1862-1869, 1990.

Hawkins, P.N., Lavender, J.P.and Pepys, M.B., Evaluation of systemic amyloidosis by scintigraphy with $^{123}$I-labeled serum amyloid P component. *N. Engl. J. Med.*, 323:508-513, 1990.

Hawkins, P.N., Myers, M.J., Epenetos, A.A., Caspi, D.and Pepys, M.B., Specific localization and imaging of amyloid deposits in vivo using $^{123}$I-labeled serum amyloid P component. *J Exp.Med.*, 167: 903-913, 1988.

Hawkins, P.N., Tennent, G.A., Woo, P.and Pepys, M.B., Studies in vivo and in vitro of serum amyloid P component in normals and in a patient with AA amyloidosis. *Clin.Exp.Immunol.*, 84:308-316, 1991.

Hind et al., "Binding specificity of serum amyloid P component for the pyruvate acetal of galactose", *J. Exp. Med.* 159, 1058-1069, 1984.

Hind et al., "Specific chemical dissociation of fibrillar and non-fibrillar components of amyloid deposits", *Lancet*, pp. 376-378, Aug. 18, 1984.

Hind, C.R.K., Collins, P.M., Baltz, M.L.and Pepys, M.B. (1985) Human serum amyloid P component, a circulating lectin with specificity for the cyclic 4,6-pyruvate acetal of galactose. Interactions with various bacteria. *Biochem.J.* 225: 107-111.

Hintner, H., Booker, J., Ashworth, J.,Aubock, J., Pepys, M.B.and Breathnach, S.M., Amyloid P component binds to keratin bodies in human skin and to isolated keratin filament aggregates in vitro. *J. Invest. Dermatol.*, 91:22-28, 1988.

Hohenester et al., "Crystal structure of a decameric complex of human serum amyloid P component with bound dAMP", *J. Mol. Biol. 269*, 570-578, 1997.

Holmgren et al., Biochemical effect of liver transplantation in two Swedish patients with familial amyloidotic polyneuropathy (FAP-met[30]), *Clin. Genet. 40*, 242-246, 1991.

Holmgren et al., "Clinical improvement and amyloid regression after liver transplantation in hereditary transthyretin amyloidosis", *Lancet*, pp. 1113-1116, May 1, 1993.

Hutchinson et al., "Human serum amyloid P component is a single uncomplexed pentamer in whole serum", *Mol. Med.* 6(6), 482-493, 2000.

Hutchinson et al., "The petraxins, C-reactive protein and serum amyloid P component, are cleared and catabolized by hepatocytes in vivo", *J. Clin. Invest. 94*, 1390-1396, 1994.

International Search Report for PCT/GB 02/03504.

International Search Report for PCT/GB2004/002445.

Iversen, "Amyloid diseases: Small drugs lead the attack," *Nature*, 414, 231-233, 2002.

Kelly, "The role of glucosamine sulfate and chondroitin sulfates in the treatment of degenerative joint disease," *Altern. Med. Rev.* 3, 27-39, 1998.

Klabunde et al., "Rational design of potent human transthyretin amyloid disease inhibitors", *Nature Struct. Biol.* 7(4), 312-321, 2000.

Ladefoged, C., Amyloid deposits in human hip joints. A macroscopic, light and polarization microscopic and electron microscopic study of congophilic substance with green dichroism in hip joints. *Acta Path. Microbiol. Immunol. Scand. Sect.*, 90:5-10, 1982.

Ladefoged, C., Amyloid in osteoarthritic hip joints: deposits in relation to chondromatosis, pyrophosphate, and inflammatory cell infiltrate in the synovial membrane and fibrous capsule. *Ann. Rheum. Dis.*, 42: 659-664, 1983.

Ladefoged, C., Christensen, H.E.and Sorensen, K.H., Amyloid in osteoarthritic hip joints. Deposition in cartilage and capsule. Semiquantitative aspects. *Acta Orthop .Scand.*, 53:587-590, 1982.

Ladefoged, C.,Amyloid deposits in the knee joint at autopsy. *Ann. Rheum.Dis.*, 45:668-672, 1986.

Lakhanpal, S., Li, C.Y., Gertz, M.A., Kyle, R.A.and Hunder, G.G., Synovial fluid analysis for diagnosis of amyloid arthropathy. *Arthritis Rheum.*, 30:419-423, 1987.

Lindorfer etal., "A bispecific dsDNAXmonoclonal antibody construct for clearance af anti-dsDNA IGG in systemic lupus erythematosus", *J. Immunol. Methods 248*, 125-138, 2001.

Liu et al., "Protein heterodimerization through ligand-bridged multivalent pre-organization: enhancing ligand binding toward both protein targets," *J.Am.Chem.Soc.127*, 2044-2045, 2005 (published on the web Jan.27, 2005).

Mitrovic, D.R., Stankovic, A., Quintero, M. and Ryckewaert, A.(1985) "Amyloid deposits in human knee and hip joints." *Rheumatol. Int.*, 5:83-89.

Natchus et al., "Development of new hydroxamate matrix metalloproteinase inhibitors derived from functionalized 4-aminoprolines," *J. Med. Chem. 43*, 4948-4963, 2000.

Nelson et al., "Serum amyloid P component in chronic renal failure and dialysis", *Clinica Chimica Acta 200*, 191-200, 1991.

Nelson, S.R., Hawkins, P.N., Richardson, S., Lavender, J.P., Sethi, D., Gower, P.E., Pugh, C.W., Winearls, C.G., Oliver, D.O.and Pepys, M.B., Imaging of haemodialysis-associated amyloidosis with $^{123}$I-serum amyloid P component. *Lancet*, 338: 335-339, 1991.

Nelson, S.R., Lyon, M., Gallagher, J.T., Johnson, E.A.and Pepys, M.B., Isolation and characterization of the integral glycosaminoglycan constituents of human amyloid A and monoclonal light-chain amyloid fibrils. *Biochem. J.*, 275:67-73, 1991.

Noursadeghi, M., Bickerstaff, M.C.M., Gallimore, Jr., Herbert, J., Cohen, J. and Pepys, M.B. Role of serum amyloid P component in bacterial infection: protection of the host or protection of the pathogen. *Proc. Natl. Acad. Sci. USA*, 97: 14584-14589, 2000.

Osmand, A.P., Friedenson, B., Gewurz, H., Painter, R.H., Hofmann, T. and Shelton,E. Characterisation of C-reactive protein and the complement subcomponent Clt as homologous proteins displaying cyclic pentameric symmetry (pentraxins).*Proc. Natl. Acad. Sci.USA*, 74: 739-743. 1977.

Paul et al., "Identification of optimal anion spacing for anti-HIV activity in a series of cosalane tetracarboxylates", *Bioorg. Med. Chem. Lett.* 10(18), 2149-2152, 2000.

Pepys et al., "Amyloid P component. A critical review.", *Int. J. Exp. Clin. Invest. 4*, 274-295, 1997.

Pepys et al., "Human lysozyme gene mutations cause hereditary systemic amyloidosis", *Nature 362*, 553-557, 1993.

Pepys et al., "Human serum amyloid P component is an invariant constituent of amyloid deposits and has a uniquely homogeneous glycostructure", *Proc. Natl. Acad. Sci. USA 91*, 5602-5606, 1994.

Pepys et al., "Isolation of amyloid P component (Protein AP) from normal serum as a calcium-dependent binding protein", *Lancet*, pp. 1029-1031, May 14, 1977.

Pepys et al., "Molecular mechanisms of fibrillogenesis and the protective role of amyloid P component: two possible avenues for therapy", *The Nature and Origin of Amyloid Fibrils (Ciba Foundation Symposium 199)* John Wiley and Sons, Chichester, 1996, pp. 73-89.

Pepys et al., "Targeted pharmacological depletion of serum amyloid P component for treatment of human amyloidosis", *Nature 417*, 254-259, 2002.

Pepys, "C-reactive protein and amyloidosis: from protein to drugs?", The Lumleian Lecture, In Horizons in Medicine, vol. 10, G. Williams, editor, pp. 397-414, 1999.

Pepys, M.B., Dyck, R.F., de Beer, F.C., Skinner, M.and Cohen, A.S., Binding of serum amyloid P component (SAP) by amyloid fibrils. *Clin. Exp. Immunol.*, 38:284-293, 1979.

Pepys, M.B.and Baltz, M.L. Acute phase proteins with special reference to C-reactive protein and related proteins (pentaxins) and serum amyloid A protein. *Adv. Immunol.*, 34: 141-212, 1983.

Pepys, M.B.and Butler, P.J.G., Serum amyloid P component is the major calcium-dependent specific DNA binding protein of the serum. *Biochem. Biophys. Res. Commun.*,148:308-313, 1987.

Pontet et al., "One step preparation of both human C-creative protein and Cit", *FEBS Letters* 88(2), 172-175, 1978.

Purkey et al., "Evaluating the binding selectivity of transthyretin amyloid fibril inhibitors in blood plasma", *Proc. Natl. Acad. Sci. USA* 98(10), 5566-5571, 2001.

Riedstra et al., "Study of an anti-human transthyretin immunoadsorbent—influence of coupling chemistry on binding capacity and ligand leakage", *J. Chromatogr. B: Biomedical Sciences & Applications*. 705(2), 213-222, 1998.

Shaker et al., "Effect of low molecular weight heparin and different heparin molecular weight fractions on aggrecanase activity: structure-function relationship," *Blood* 100(11), Abstract No. 3849, 2002.

Solomon et al., Heterobifunctional Multivalent Inhibitor-Adaptor Mediates Specific Aggregates between Shiga Toxin and a Pentraxin, *Organic Letters*, American Chemical Society, 7(20), pp. 4369-4372, 2005.

Sorensen, K.H., Stubbe Teglbjaerg, P., Ladefoged, C.and Christensen, H.E., Pyrophosphate arthritis with local amyloid deposition. *Acta Orthop. Scand.*, 52:129-133, 1981.

Srinivasan, N., Rufino, S.D., Pepys, M.B., Wood, S.P.and Blundell, T.L., A superfamily of proteins with the lectin fold. *Chemtracts-Biochem. Mol. Biol.*, 6:149-164, 1996.

Srinivasan, N., White, H.E., Emsley, J., Wood, S.P., Pepys, M.B.and Blundell, T.L. Comparative analyses of pentraxins: implications for protomer assembly and ligand binding. *Structure*, 2:1017-1027. 1994.

Sukenik et al., "Serum and synovial fluid levels of serum amyloid a protein and c-reactive protein in inflammatory and noninflammatory arthritis" *J. of Rheumatology* 15(6), 942-945, 1988.

Sunde, M., Serpell, L.C., Bartlam, M., Fraser, P.E., Pepys, M.B.and Blake, C.C.F., Common core structure of amyloid fibrils by synchrotron X-ray diffraction. *J. Mol. Biol.*, 273: 729-739, 1997.

Takeda, T., Sanada, H., Ishii, M., Matsushita, M., Yamamuro, T.,Shimizu, K. and Hosokawa, M., Age-associated amyloid deposition in surgically-removed herniated intervertebral discs. *Arthritis Rheum.*, 27:1063-1065, 1984.

Tan, S.Y., Baillod, R., Brown, E., Farrington, K., Soper, C., Percy, M., Clutterbuck, E., Madhoo, S., Pepys, M.B. and Hawkins, P.N., Clinical, radiological and serum amyloid P component scintigraphic features of $\beta$-microglobulin amyloidosis associated with continuous ambulatory peritoneal dialysis. *Nephrol. Dial. Transplant.*, 14:1467-1471, 1999.

Tennent et al., "Serum amyloid P component prevents proteolysis of the amyloid fibrils of Alzheimer disease and systemic amyloidosis", *Proc. Natl. Acad. Sci. USA 92*, 299-4303, 1995.

Tennent, G.A., Butler, P.J.G., Hutton, T., Woolfit, A.R., Harvey, D.J., Rademacher, T.W.and Pepys, M.B., Molecular characterization of *Limulus* polyphemus C-reactive protein. I.Subunit composition. *Eur. J. Biochem.*, 214:91-97, 1993.

Ying, S.-C., Gewurz, A.T., Jiang, H.and Gewurz, H., Human serum amyloid P component oligomers bind and activate the classical complement pathway via residues 14-26 and 76-92 of the A chain collagen-like region of Clq. *J. Immunol.*, 150:169-176 1993.

Nishukaku et. al.,"Protective Effects of D-Penicillamine and a Thiazole Derivative, SM-8849, on Pristane-Induced Arthritis in Mice," International Journal of Immunopharmacology, vol. 16, No. 2 pp. 91-100.

Danielsen et. al., "Calcium-dependent and -independent binding of the pentraxin serum amyloid P component to glycosaminoglycans and amyloid proteins: enhanced binding at slightly acid pH," Biochimica et Biophysica Acta 1339 (1997) 73-78.

Kosack, Joseph R., Office Action Mailed Jun. 2, 2009 for U.S. Appl. No. 11/332,312, United States Patent and Trademark Office.

COMPOUNDS INHIBITING THE BINDING OF SAP FOR TREATING OSTEOARTHRITIS

This is a U.S. national stage of Intl. Patent Appl. No. PCT/GB04/002445, filed 10 Jun. 2004, which claims priority to Great Britain Patent Appl. No. 0313386.5, filed 10 Jun. 2003.

FIELD OF THE INVENTION

The present invention relates to the treatment or prevention of osteoarthritis.

BACKGROUND TO THE INVENTION

Osteoarthritis is the commonest form of arthritis and is detectable radiologically in 80% of individuals over the age of 55 in Western populations. Symptomatic osteoarthritis of the knee, that is pain with radiographic abnormalities, is present in about 6% of individuals over the age of 30 in both the USA and the UK. In the USA approximately 21 million people have physician diagnosed osteoarthritis, most of whom have significant pain and disability. Indeed, in some 12% of all subjects with limitation of activity, the cause is osteoarthritis, and it accounts for more dependency in walking and stair climbing than any other disease. The estimated annual cost of osteoarthritis in the USA is $15.5 billion in 1994 dollars, which approaches 1% of the GNP, with more than 50% of the costs due to work loss. The problem is inevitably becoming more severe with an ageing population and the clear age related incidence of osteoarthritis (1).

The pathology of osteoarthritis comprises loss of articular cartilage and complex processes of repair with fibrocartilage and reactive bone formation, leading to disruption of normal joint and peri-articular architecture. This is associated with pain, synovial effusions and loss of function.

Traditional treatments are: weight loss, exercise and psychosocial support; simple analgesics; non-steroidal anti-inflammatory drugs; intra-articular corticosteroids; hyaluronic acid; joint lavage; physical aids and appliances. However these conservative approaches are inadequate in a significant proportion of patients for whom surgery then becomes appropriate, including synovectomy, repair of meniscal tears, realignment osteotomy, and eventually total joint replacement. Only the latter is a cure for osteoarthritis, and obviously it is only applicable to some joints and some individuals.

Other experimental and less well validated therapeutic approaches include administration of glucosamine and chrondroitin sulphate, ostensibly to promote survival or even repair of damaged cartilage, and tetracycline, interleukin-1 antagonists and inhibitors of collagenase and other matrix proteinases.

There is thus clearly an enormous need for new medications that can modify progression of osteoarthritis, and, importantly, alleviate its distressing and incapacitating symptoms of pain, joint deformity and effusions, limitation of activity and disability.

Serum amyloid P component (SAP) is a member of the conserved and evolutionarily ancient pentraxin family (2) of plasma proteins, the other member of which is C-reactive protein (CRP) the classical acute phase protein (3). Homologous proteins that share the same 3D fold (4,5), oligomeric assembly and capacity for calcium-dependent ligand binding, are present in all vertebrates (6) and even in the horseshoe crab, Limulus polyphemus (7), that is separated in evolution from primates by about 600 million years. No deficiency or protein polymorphism of SAP have been described yet in humans, and its carbohydrate component is the most invariant of any known glycoprotein (8). This is all compelling evidence that SAP has beneficial functions that contribute to survival.

However, SAP derives its name from the fact that it is universally present in the pathological tissue deposits of amyloid in the disease state of amyloidosis (9). The bulk of these deposits consists of amyloid fibrils composed of autologous protein misfolded and aggregated with a pathognomonic cross-β fold (10), together with tightly bound glycosaminoglycans of heparan sulphate and dermatan sulphate types (11). SAP undergoes specific calcium-dependent binding to these fibrils, both in vitro (12) and in vivo (13,14), and this property has been exploited to develop radiolabelled SAP as a highly specific, sensitive and quantitative in vivo scintigraphic tracer for diagnosis and monitoring of the deposits in systemic and local extra-cerebral amyloidosis (15).

One of the forms of local extra-cerebral amyloidosis that is of the greatest clinical importance is dialysis associated amyloidosis, a very serious, painful and crippling complication of long term dialysis for end stage renal failure. This type of amyloid is largely confined to joints and peri-articular structures, producing nerve compression, and bone cysts leading to disruption of joints and pathological fractures. Dialysis amyloidosis has been studied extensively using radiolabelled SAP, showing that uptake in and around joints is specific for histologically proven amyloid deposits in these locations (16, 17).

Drugs which are bound by SAP have been developed for the purpose of treating amyloidosis, including Alzheimer's disease. WO95/05394 describes therapeutic and diagnostic agents for amyloidosis which comprise molecules that inhibit the binding of SAP to amyloid fibrils. EP-A-0915088 describes D-prolines and derivatives thereof for use in the treatment or prevention of central and systemic amyloidosis including Alzheimer's disease, and maturity onset diabetes mellitus. WO03/013508 describes therapeutic agents for depletion of unwanted protein populations from plasma in which bifunctional agents form a complex with a plurality of proteins to deplete them from the plasma of a subject. It is disclosed that R-1-[6-R-2-carboxy-pyrrolidin-1-yl]-6-oxo-hexanoyl]pyrrolidine-2-carboxylic acid specifically targets SAP in vivo to cause aggregation of native pentameric SAP molecules into decameric SAP-drug complexes that are then swiftly cleared by the liver.

SUMMARY OF THE INVENTION

The present invention relates to the use of an agent for the production of a medicament for treatment or prevention of osteoarthritis in a subject. The agent is capable of inhibiting SAP ligand binding activity or capable of depleting SAP from the plasma of the subject.

It has surprisingly been found that the use of such agents to treat patients with osteoarthritis has a dramatic effect in relieving symptoms of the disease in patients.

In a first aspect, the agent is capable of inhibiting SAP ligand binding activity. Agents capable of inhibiting SAP ligand binding activity include those which are capable of being bound by a ligand binding site present on SAP and those which may be bound elsewhere and yet block or inhibit SAP ligand binding activity. Accordingly, inhibition of SAP ligand binding activity may arise by direct inhibition or by allosteric inhibition. The inhibition may be competitive or non-competitive and may be reversible or irreversible.

A general method for selecting an agent capable of inhibiting SAP ligand binding activity for use in the treatment or prevention of osteoarthritis comprises contacting serum amyloid P component (SAP) with a target ligand thereof under conditions to permit SAP ligand binding, in the presence of a test compound; testing for SAP ligand binding; and selecting the test compound as an SAP inhibitor if the test compound inhibits binding of SAP to the target ligand.

The present invention further provides a process for the production of an anti-osteoarthritis agent, which process comprises (i) identifying an SAP inhibitor by selecting the compound according to the above method; and (ii) producing an anti-osteoarthritis agent by providing the SAP inhibitor or a pharmaceutically-acceptable derivative thereof.

The present invention is therefore concerned in one embodiment with a method for selecting an SAP inhibitor which includes testing for SAP ligand binding in the presence of a test compound. Any test compound which inhibits binding of SAP to the ligand may be selected as an inhibitor. For example, the test compound may be selected in the sense that it is identified and can then be produced on a larger scale by chemical or biochemical synthesis or may be physically selected for direct formulation as an anti-osteoarthritis agent. In accordance with the process for production of the agent, the test compound may be formulated for pharmaceutical use or may be derivatised or chemically modified to produce a pharmaceutically-acceptable derivative thereof. Such derivatisation may simply be required to incorporate new functional groups or alter existing functional groups to make the agent easier to formulate, for example by altering the solubility of the compound. Derivatisation of this nature may be used to decrease the toxicity of the compound, to alter the stability of the compound or even to modify the pharmacological activity thereof. Any such derivatised or modified compound may need to be retested according to the method of the present invention.

In the step of contacting SAP with the ligand, the conditions must be sufficient to permit SAP ligand binding in the absence of the test compound. In this way, where SAP ligand binding does not occur in the presence of the test compound, or occurs to a smaller extent than expected, this effect can be attributed to the test compound. It should be noted here that inhibition of binding should be broadly construed and is not limited to any particular mechanism; any reduction of the extent of binding constitutes inhibition of binding according to the present invention. Inhibition of binding is generally measured with reference to a control value (maximum binding in absence of test compound) and it is preferred that the $IC_{50}$ be low micromolar or less, more preferably nanomolar or less. Contacting takes place under conditions which include sufficient free calcium ions to permit the specific calcium dependent binding of SAP. In addition, it is necessary to ensure a sufficient amount of serum albumin to prevent the calcium-dependent autoaggregation that is characteristic of isolated SAP (18,19). A preferred buffer for the contacting is physiological buffered saline. SAP may be provided in isolated pure form or incorporated in whole serum.

Suitable ligands to which SAP binds include materials of human or other mammalian origin, materials originating from lower animals or of microbial origin, and synthetic materials. Macromolecular ligands include DNA, chromatin, amyloid fibrils, glycosaminoglycans (specifically heparin, heparan and dermatan sulphates) and agarose and other carbohydrates bearing the carboxyethylidene ring that is specifically recognised by SAP. Synthetic ligands include phosphoethanolamine groups immobilised by covalent carbodiimide coupling to carboxyl groups attached to a solid phase. With appropriate solid materials that bear ligands, such as some micro-organisms, whole organisms such as bacteria can be used, thereby conveniently avoiding the need for purification of the actual ligand molecule(s). Suitable bacteria to which SAP avidly binds include Streptococcus pyogenes (20) and Neisseria meningitidis (21). The most suitable virus bearing ligands for SAP is the human influenza virus (22).

The order in which the SAP, target ligand and test compound are contacted together is not critical. All three components can be mixed at essentially the same time or two of the three components can be mixed and perhaps pre-incubated before addition of the third component. Contacting generally takes place under conditions in which at least one of the components is in the liquid phase. It is convenient, however, for either the SAP or the ligand to form part of a solid phase so that, in the testing procedure, phase separation can be used as a technique to separate bound species from unbound species to facilitate testing for the extent of SAP ligand binding.

Accordingly, it is preferred that a first component comprising one of SAP or the ligand is present as part of a solid phase, which is contacted with a second component comprising the other as part of a liquid phase. The step of testing for SAP ligand binding may then comprise detecting binding of the second component to the solid phase. Detecting binding of the second component to the solid phase may be effected either by detecting the presence of the second component on the solid phase or by determining the amount of second component unbound to the solid phase and deducing from the amount of second component originally applied to the solid phase the amount actually binding to the solid phase.

According to this embodiment, the solid phase preferably comprises the first component attached to a solid support, which solid support may comprise a particulate support or a solid surface. In a convenient embodiment, the solid surface comprises an interior surface of the container such as a microtitre plate well.

Conveniently, the step of testing for SAP ligand binding further comprises washing the solid phase to remove unbound material.

The second component may be labelled with a detectable label such as a radiolabel, a fluorochrome or an enzyme, as discussed herein. Alternatively, the binding of the second component to the solid phase may be detected immunologically either by antibody binding to the second component as bound to the solid phase or by quantitative immunological determination of the amount of second component not bound to the solid phase.

The present invention provides in vitro spot tests, low throughput, and high throughput screening procedures for detecting compounds with the capacity to inhibit binding of SAP, from man or other animals, to target ligands. These methods are suitable for screening test compound libraries of natural compounds of organic, inorganic and biological origin, as well as chemical libraries created by conventional synthesis or any form of combinatorial chemistry. They are also suitable for analysis of the mechanism of inhibition of SAP binding, and for evaluation of potency of inhibition during chemical and medicinal chemistry development of potential or actual pharmaceutical products from lead compounds identified by screening or spot testing. The present invention also provides in vivo methods for testing effects and potency of SAP-inhibitory compounds on SAP binding, plasma turnover and catabolism in man and experimental animals.

In a further embodiment, the present invention provides a method for selecting an anti-osteoarthritis compound from a plurality of test compounds, which comprises providing an array of reaction zones and a plurality of test compounds, contacting in each reaction zone SAP with a ligand thereof under conditions to permit SAP ligand binding, in the presence of one of the test compounds; testing for SAP ligand binding in each reaction zone; and selecting as an anti-osteoarthritis compound any test compound which inhibits binding of SAP to the ligand.

This method is suitable for a high throughput screening procedure in which the plurality of test compounds comprises a library of test compounds for screening. By providing an array of reaction zones and a plurality of test compounds, the anti-osteoarthritis compound may be selected by performing the method of the present invention in each reaction zone. This enables the method of the present invention to be scaled up for high throughput and can be performed by automated or semi-automated apparatus such as that based on an array of containers such as a microtitre plate well array.

Suitable compounds may be bound by SAP and thereby block the site of interaction between SAP and the ligand, or they may bind to SAP to alter its structure thereby to inhibit or prevent binding to the ligand. It is known that the SAP molecule has a specific calcium-dependent ligand binding site through which it binds to ligand. A major class of compounds that can be identified using the present invention comprises substances that are bound by the calcium-dependent ligand binding site of SAP so as to interfere with binding of SAP to the ligand. However the present invention also provides for detection and study of compounds that inhibit SAP binding by the other mechanisms listed above.

Test compounds useful according to the present invention include those candidate compounds described in WO95/05394. This PCT application describes the complete resolution of the three-dimensional structure of SAP by X-ray crystallography. The binding of SAP in vitro to amyloid fibrils is also demonstrated, whereby proteolytic degradation of those fibrils in the presence of proteinases is prevented. This protection by SAP may be abrogated by compounds capable of inhibiting SAP ligand binding activity. Such compounds may therefore be detected by an assay as described in WO95/05394. Candidate test compounds for that assay or for the screening methods described herein may be provided by knowledge of the structure of the ligand binding site identified in WO95/05394. The PCT application also provides a method for the production of a molecule that inhibits the binding of SAP to amyloid fibrils. The method comprises carrying out computer-aided molecular design using the three-dimensional structure of SAP, synthesising the molecules thus designed and testing the molecules for the ability to inhibit binding of SAP to amyloid fibrils and/or the ability to bind to amyloid fibrils. Molecules according to WO95/05394 may therefore be molecules which interact with SAP at and/or around the calcium binding site illustrated therein. Such a molecule may, for example, interact with one or more of the residues Asp58, Asn59, Glu136 Asp138 and Gln37 of human SAP or with the equivalent residues in SAP from another species and/or with one or more basic residues in the region of those residues. Molecules of WO95/05394 may form hydrogen bonds to the hydroxyl groups of Tyr64 and Tyr75 of human SAP or the equivalent residues in SAP of another species.

In a preferred aspect, the agent comprises a substituted or unsubstituted D-proline or stereoanalogue thereof. Such agents may or may not be capable of inhibiting SAP ligand binding activity or depleting SAP from the plasma of a subject provided that they are effective for treatment or prevention of osteoarthritis in a subject. It is preferred, however, that such agents are capable of inhibiting SAP ligand binding activity or depleting SAP from the plasma of a subject. Such agents may therefore be obtainable by any one of the screening methods described herein.

A preferred group of D-proline compounds according to the invention has previously been described in EP-A-0915088. This European patent application describes a class of D-prolines which have the formula

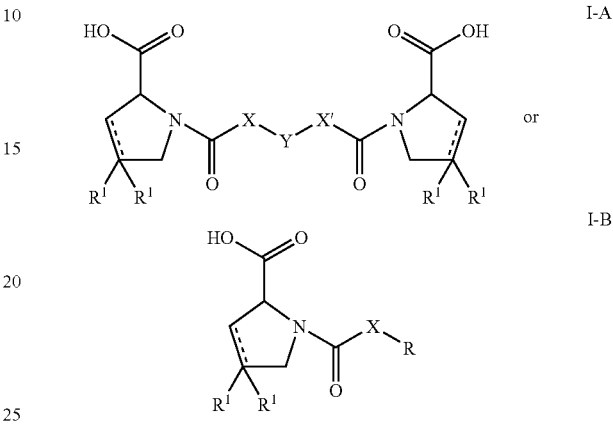

wherein
R is

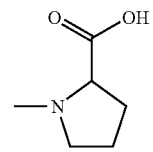

the group;
$R^1$ is hydrogen or halogen;
X is —$(CH_2)_n$—; —$CH(R^2)(CH_2)_n$—; —$CH_2O(CH_2)_n$—; —$CH_2NH$—; benzyl, —$C(R^2)$=CH—; —$CH_2CH(OH)$—; or thiazol-2,5-diyl;
Y is —S—S—; —$(CH_2)_n$—; —O—; —NH—; —$N(R^2)$—; —CH=CH—; —NHC(O)NH—; —$N(R^2)C(O)N(R^2)$—; —$N[CH_2C_6H_3(OCH_3)_2]$—; —$N(CH_2C_6H_5)$—; —$N(CH_2C_6H_5)C(O)N(CH_2C_6H_5)$—; —N(alkoxyalkyl)-; N(cycloalkyl-methyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxy, carboxy, —COO-lower alkyl, nitrilo, 5-tetrazol, (2-carboxylic acid pyrrolidin-1-yl)-2-oxo-ethoxy, N-hydroxycarbamimidoyl, 5-oxo[1,2,4]oxadiazolyl, 2-oxo-[1,2,3,5]oxathiadiazolyl, 5-thioxo[1,2,4]oxadiazolyl and 5-tert-butylsulfanyl-[1,2,4]oxadiazolyl;
X' is —$(CH_2)_n$—; —$(CH_2)_nCH(R^2)$—; —$(CH_2)_nOCH_2$—; —$NHCH_2$—; benzyl, —CH=$C(R^2)$—; —$CH(OH)CH_2$; or thiazol-2,5-diyl;
$R^2$ is lower alkyl, lower alkoxy or benzyl and
n is 0-3, or a pharmaceutically acceptable salt or mono- or diester thereof.

Stereoanalogues of the D-prolines of this class are also included in the present invention.

According to the above formula, the term "lower alkyl" denotes straight-chain or branched-chain saturated hydrocarbon residues, preferably with 1 to 4 carbon atoms, such as methyl, ethyl, propyl, isopropyl, n-butyl, 2-butyl, isobutyl and t-butyl. Halogen denotes chlorine, iodine, fluorine and bromine. Compounds of formula 1-A and 1-B can form salts with metals, for example alkali metal salts such as sodium or potassium salts, or alkaline earth metal salts such as calcium or magnesium salts, with organic bases, for example salts with amines, such as n-ethylpiperidine, procaine or dibenzylamine, or salts with basic amine acids such as salts with arginine or lysine. The compounds can also be used in an ester form, such esters being aliphatic or aromatic. These esters include, for example, alkyl and phenolic esters. The most preferred esters are alkyl esters derived from $C_{1-4}$ alkanols, especially methyl and ethyl esters.

These compounds can also be used in the form of their prodrugs at either one or both carbonyl functions.

Details of examples of these compounds and their syntheses are described in EP-A-0915088.

Particularly preferred agents according to the present invention include those which comprise a plurality of ligands covalently co-linked so as to form a complex with SAP and a second protein, preferably SAP. At least two of the ligands are the same or different and one of which is capable of being bound by a ligand binding site present on SAP and another is capable of being bound by a ligand binding site present on the second protein. Agents of this type may be capable of inhibiting SAP ligand binding activity and/or may be capable of depleting SAP from the plasma in a subject. As described in WO03/013508 and by Pepys et al (23), such agents were found to be dramatically potent in vivo at depleting the target protein from the circulation by causing it to be rapidly cleared. It is thought that where at least one of the ligands is capable of being bound by a ligand site present on SAP and the other capable of being bound by a ligand site present on SAP or a second different protein, a complex is formed which is identified by the body's own physiological mechanisms as requiring prompt clearance and destruction. Accordingly, SAP is removed from the subject so as to effect treatment or prevention of osteoarthritis. In the compound (R)-1-[6-[(R)-2-Carboxy-pyrrolidin-1-yl]-6-oxo-hexanoyl]pyrrolidine-2-carboxylic acid (WO03/013508 and reference (23)), the carboxylate-containing pyrrolidine ring at each end is bound by the calcium dependent ligand binding site of SAP, resulting in the face-to-face cross-linking of pairs of SAP molecules, as shown by gel filtration, and by atomic resolution X-ray crystallography of the complexes. This cross-linking evidently causes SAP to be cleared from the plasma in vivo and rapidly catabolised, and this is the desired effect of compounds according to this embodiment of the present invention.

The affinity of each individual ligand-protein binding site interaction does not need to be particularly high provided that the ligand is specific for each target protein. It is possible that a dissociation constant of up to 10 millimolar would suffice. However, it is preferred that the dissociation constant is no more than 1 millimolar, more preferably less than 100 micromolar, most preferably less than 10 micromolar. The affinity is preferably about micromolar or higher. Micromolar affinity has been found to be sufficient in the case of SAP, although the highest possible affinity is clearly desirable.

In the agents of the present invention, although the ligands may be directly linked together by a covalent bond, the ligands are preferably covalently co-linked by a linker. This enables the ligands to be sufficiently spatially separated whereby a plurality of target proteins may be bound to the agent without one protein hindering the binding of the other protein or proteins. The exact structure of the linker is not critical although it is typically preferred not to include reactive groups. The linker may comprise a linear or branched hydrocarbylene which may have one or more of its carbon atoms optionally substituted by a heteroatom. The linker may have a chain length in the range 2 to 20 atoms. Useful chain length and chemical composition may be determined empirically depending on the proteins with which the agent is to be complexed. Where the agent has two ligands, the linker is typically linear; a preferred general structure is ligand-linker-ligand. This is conveniently denoted a "palindrome" for the purposes of the present application. Although other structures involving three, four or more ligands with an appropriate branched chain linker are also contemplated where three, four or more target proteins could form a complex.

Pharmaceutical compositions may be formulated comprising an agent according to the present invention optionally incorporating a pharmaceutically-acceptable excipient, diluent or carrier. The pharmaceutical compositions may be in the form of a prodrug comprising the agent or a derivative thereof which becomes active only when metabolised by the recipient. The exact nature and quantities of the components of such pharmaceutical compositions may be determined empirically and will depend in part upon the route of administration of the composition. Routes of administration to recipients include oral, buccal, sublingual, by inhalation, topical (including ophthalmic), rectal, vaginal, nasal and parenteral (including intravenous, intra-arterial, intramuscular, subcutaneous and intra-articular) For convenience of use, dosages according to the present invention are preferably administered orally but this will depend on the actual drug and its bioavailability.

According to this aspect of the invention it is preferred that the ligand capable of being bound by the ligand binding sites on SAP comprises a substituted or unsubstituted D-proline or stereoanalogue thereof. A particularly preferred D-proline is (R)-1-[6-(R)-2-Carboxy-pyrrolidin-1-yl]-6-oxo-hexanoyl] pyrrolidine-2-carboxylic acid or a pharmaceutically acceptable salt or mono- or diester thereof.

Another approach to the inhibition of SAP binding, and depletion of SAP that are desirable according to the present invention is the use of macromolecules that either are bound by, or bind to, SAP. In the first category are peptides of various sizes containing one, or preferably more that one, carboxy terminal D-proline residues and preferably composed of D-amino acids in order to resist proteolytic degradation in vivo. The ligands for SAP function in the same way as the low molecular weight compounds containing D-proline described here, in being bound by SAP, inhibiting the binding of SAP to other ligands in vivo, and promoting the accelerated clearance of SAP from the circulation with beneficial effects on osteoarthritis. SAP also recognises and binds other peptide motifs, including β-bends with aspartic acid and other residues in the apical position, and these types of peptide sequences are also therefore desirable. In the second category, macromolecules that bind to SAP and deplete it may comprise antibodies specific for human SAP, and for the presently desired therapeutic purpose these preferably are monoclonal antibodies that are preferably either humanised or are entirely human, or are lower molecular weight fragments of antibody molecules, such as Fv fragments, that retain their specific binding capacity for SAP. These moieties recognise and bind to SAP in vivo after administration by parenteral injection, and promote the accelerated clearance and depletion of SAP from the circulation. Generally, antibodies to SAP useful according to the present invention should not activate complement, in order to avoid potentially harmful pro-inflammatory effects when they bind to SAP in vivo. They also should preferably not recognise, bind to and damage the normal tissue structures in the body that bear SAP molecules.

BRIEF DESCRIPTION OF THE DRAWINGS

The present invention will now be described in further detail by way of example only, with reference to the following Examples and to the accompanying drawings, in which.

DETAILED DESCRIPTION OF THE INVENTION

Examples

Figure 1:
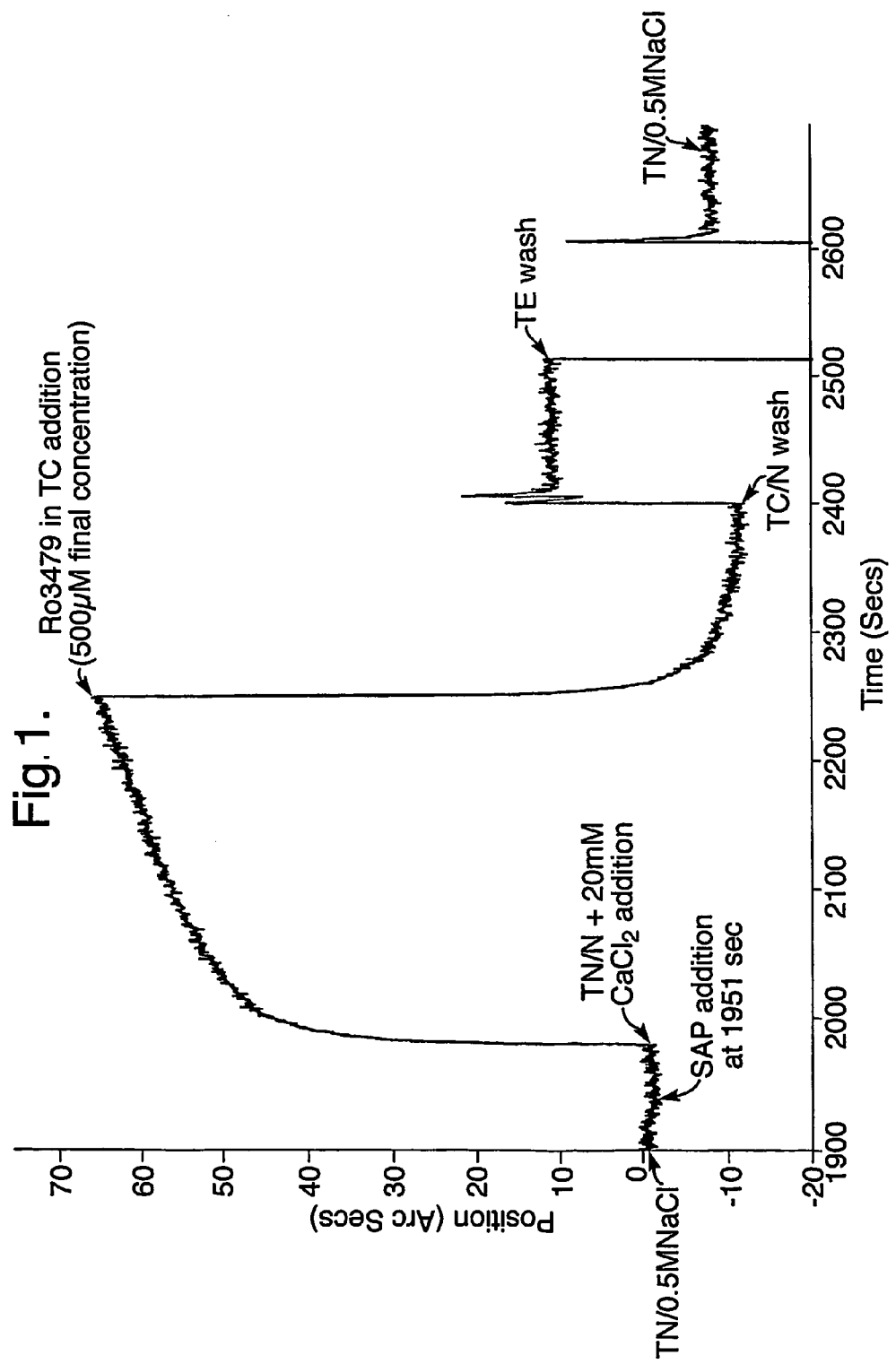
FIGS. 1 to 3 show traces from surface plasmon resonance experiments assessing the effect of 1-[(S)-3-Mercapto-2-methylpropionyl]-D-proline (designated Ro-3479 on these figures) on binding of SAP to amyloid fibrils in the presence and absence of calcium.

Methods for Showing Binding of SAP to Ligands

In order to identify compounds that inhibit ligand binding of SAP it is first necessary to have methods for showing such binding.

1] Binding of SAP to Solid Phase Ligands.

For the purposes of this invention, the binding of SAP to test ligands can be demonstrated directly by allowing SAP, provided either by whole human or animal serum, or in isolated purified form, to contact the solid phase ligand. Contact takes place in physiological buffered saline containing sufficient free calcium ions (about 2 mmol/l), which are essential for ligand binding by SAP. In the case of isolated human SAP, the buffer must also contain 40 g/l of human or bovine serum albumin, in order to keep the SAP in solution; at lower albumin concentrations isolated human SAP rapidly autoaggregates and precipitates in the presence of calcium (18,19). Suitable ligands to which SAP shows its typical calcium dependent binding include agarose (24), phosphoethanolamine (25), DNA (26), chromatin (27), and amyloid fibrils (12,28). They are immobilized on particles, such as agarose, acrylamide, polystyrene, latex, cellulose, or other beads, or on membranes, filters, or plastic or other solid surfaces such as microtitre plates or individual tubes, or may be integral components of solid particles, such as bacteria or agarose gel, that can be used directly. Immobilization of soluble ligands, or secondary immobilization of particulate ligands for purposes of convenience, may be by direct non-specific adherence of the ligand, or by covalent attachment via amino, hydroxyl, or other chemical groups on the ligand molecules being coupled directly or via spacer linkers to the solid phase material. After contacting the solid or immobilised ligands, SAP that has not bound is washed away with the same buffer in which binding took place, and the presence of SAP bound to the ligands is detected and quantified. Washing involves phase separation, such as centrifugation of solid particles, or immersion, flow through or flow over of solid surfaces such as membranes, filters, and plastic surfaces. Bound SAP may be detected directly if the source of SAP contains SAP that has been labelled with a detectable marker. Such markers include gamma-emitting isotopes such as $^{125}$I or $^{131}$I for detection in a gamma counter; beta-emitting isotopes such as $^{14}$C or $^{3}$H for detection in a beta or scintillation counter; fluorochromes for detection in a fluorimeter, flow cytometer, or fluorescence activated cell sorter; enzymes such as peroxidase or alkaline phosphatase for detection by their specific catalytic activity. In all of these cases it is essential to demonstrate that the process of directly labelling the SAP does not alter its physiological binding properties. This is done by comparing the binding of labelled and unlabelled SAP to an immobilised solid phase ligand, such as phosphoethanolamine attached using a carbodiimide to carboxyhexyl-Sepharose™. Binding of SAP can also be demonstrated directly by immunochemical assay showing depletion of SAP from the offered source of SAP, and recovery of the bound SAP when, after first washing with calcium containing buffer, the ligand material is eluted with buffer containing EDTA to chelate calcium ions. Alternatively, bound SAP may be detected indirectly, using antibodies raised in rabbits, sheep, goats, rats, mice, guinea pigs or other animals, specific for the SAP of the species being tested. For this purpose the anti-SAP antibodies may themselves be directly labelled with a radioactive isotope, enzyme, fluorochrome or other detectable marker, or the binding of anti-SAP antibodies to bound SAP may be detected using a second antibody directed against the immunoglobulin of the species of the primary anti-SAP reagent. In addition to detection and counting in instruments appropriate for the marker used, binding of SAP to micro-organisms or their components may be visualised directly or indirectly using light, fluorescence or electron microscopy. Enzyme labelled SAP or anti-SAP antibodies can be used for light or electron microscopy, fluorochrome labelled reagents for fluorescence microscopy, and gold (or other electron dense particle) labelling for electron microscopy.

2] Binding of Ligands by Immobilized SAP.

An alternative approach to demonstration of ligand binding by SAP is to immobilize the SAP on a solid phase and then allow it to bind ligands that are either directly labelled or that can be detected, for example using specific antibodies directed against these ligands. Thus isolated purified SAP from man or other animals can be immobilized on beads, particles, membranes, filters, or plastic or other solid surfaces, by direct non-specific adherence or by covalent coupling, or by trapping with specific anti-SAP antibodies immobilized on the solid phase (29). Using the conditions specified in 1] above, suitable ligands, can then be contacted to the immobilized SAP and allowed to be bound by it.

Inhibition of SAP Binding to Ligands

Any of the methods set out in 1] and 2] above for showing ligand binding by SAP can be used to test the capacity of compounds to inhibit such binding. However the speed and ease of use of the different techniques vary greatly, as well as their suitability for different purposes. Thus for screening large numbers of compounds, high throughput methods, such as those based on microtitre plates, are essential. A typical method of this type involves having ligand immobilized on the plates, and offering to each well an amount of radiolabelled SAP under conditions such that about 40% of it is bound. Compounds to be tested are added to the wells and preincubated in them before addition of the labelled SAP, and the effect of their presence on subsequent binding of SAP is monitored. In another configuration, the compounds to be tested are preincubated with the labelled SAP before the mixture is added to the plates. The reverse configuration, in which the SAP is immobilized, is also informative. Here the test compounds are preincubated with the immobilized SAP before the detectable ligand is added. These different approaches enable detection of compounds that block ligand binding by SAP by different mechanisms, and help to distinguish between those that are themselves specific ligands for SAP, those that affect the SAP molecule in other ways, and those that interact with the ligand to prevent its recognition by SAP.

Direct Detection of Ligand Binding by SAP and its Inhibition

Surface plasmon resonance (SPR) is a low throughput but powerfully informative method to identify compounds that are bound by, or themselves bind to SAP, either in a calcium dependent fashion or independently of calcium, for the purposes of the present invention. For example, low molecular weight compounds that inhibit binding of SAP to its macromolecular ligands, including target ligands relevant to the present invention, can be detected by their effect on the signal generated by fluid phase SAP binding to ligand immobilised on the solid phase (Example A). Furthermore, when SAP itself is immobilised on the solid phase in an SPR instrument, the interaction with it of test molecules provided in the fluid phase generates a signal that can be detected and quantified. Purified SAP immobilized within an SPR instrument gives a quantifiable signal when it is exposed to another molecule that forms a complex with the SAP, and this is distinct from the absence of such a signal if no complex is formed. This technique allows compounds to be screened for their capacity to interact with SAP, and does not depend on any specific mode of interaction with SAP, in particular involving the calcium dependent ligand binding site of SAP, so it detects molecules that might not be found in test systems that require calcium dependent SAP binding. Another low throughput but powerful direct method is isothermal calorimetry that measures the heat of interaction in solution between SAP and test compounds according to the present invention. The binding affinity can be measured precisely as a guide to potential efficacy. Typical results by this method for the dissociation constants, $K_d$, between SAP and various compounds are as follows:

| Compound | $K_d$ in micromoles per liter (replicate measurements) |
| --- | --- |
| Phosphoethanolamine | 36, 27, 48 |
| Phosphocholine | No binding |
| N-acetyl-D-proline | 16, 23, 17 |
| Ro-63-8695 | 0.0139, 0.0059, 0.0065, 0.0088 |
| Ro-64-2856 | 0.019, 0.02 |

The latter two compounds are from EP-A-915088, in which Ro-63-8695 is (R)-1-[6-[(R)-2-Carboxy-pyrrolidin-1-yl]-6-oxo-hexanoyl]pyrrolidine-2-carboxylic acid, and Ro-64-2856 is (R)-1-[[4-[2-[(R)-2-Carboxy-pyrrolidin-1-yl]-2-oxo-ethoxy]-phenoxy]-acetyl]-pyrrolidine-2-carboxylic acid.

Effects on SAP In Vivo of Compounds that Block SAP-Ligand Binding In Vitro.

For the purpose of the present invention, compounds that block binding of SAP to target ligands are tested in vivo in transgenic mice expressing human SAP, as described elsewhere (23) for their effects on plasma SAP concentrations and the turnover and catabolism of SAP. Having established by the administration of graded doses that the compounds are not intrinsically toxic, various doses are administered to the human SAP transgenic mice. Serum is taken at regular intervals for immunochemical assay of SAP. In addition, trace radiolabelled human SAP may be injected intravenously at different times in relation to the drug dosage, and both whole body counting and blood sampling are performed to monitor the plasma half life and whole body clearance of SAP (14,30). In addition the tracer SAP is preincubated with different amounts of the compounds being tested, and then injected into mice not receiving any drug, in order to test the effect drug binding has on SAP clearance. According to the present invention, compounds that accelerate SAP clearance in vivo and/or lower plasma SAP concentration, thereby reducing in vivo availability of SAP, are likely to be of therapeutic value.

Compounds that have undergone formal toxicity testing and found to be acceptable for administration in man, are evaluated for their effects on plasma SAP concentration, half life, turnover and catabolism. Isolated human SAP is trace radiolabelled with $^{125}$I and/or $^{123}$I and injected intravenously, followed by plasma turnover studies and whole body scintigraphic imaging, as described elsewhere (15,23,31).

Example A

Figure 2:
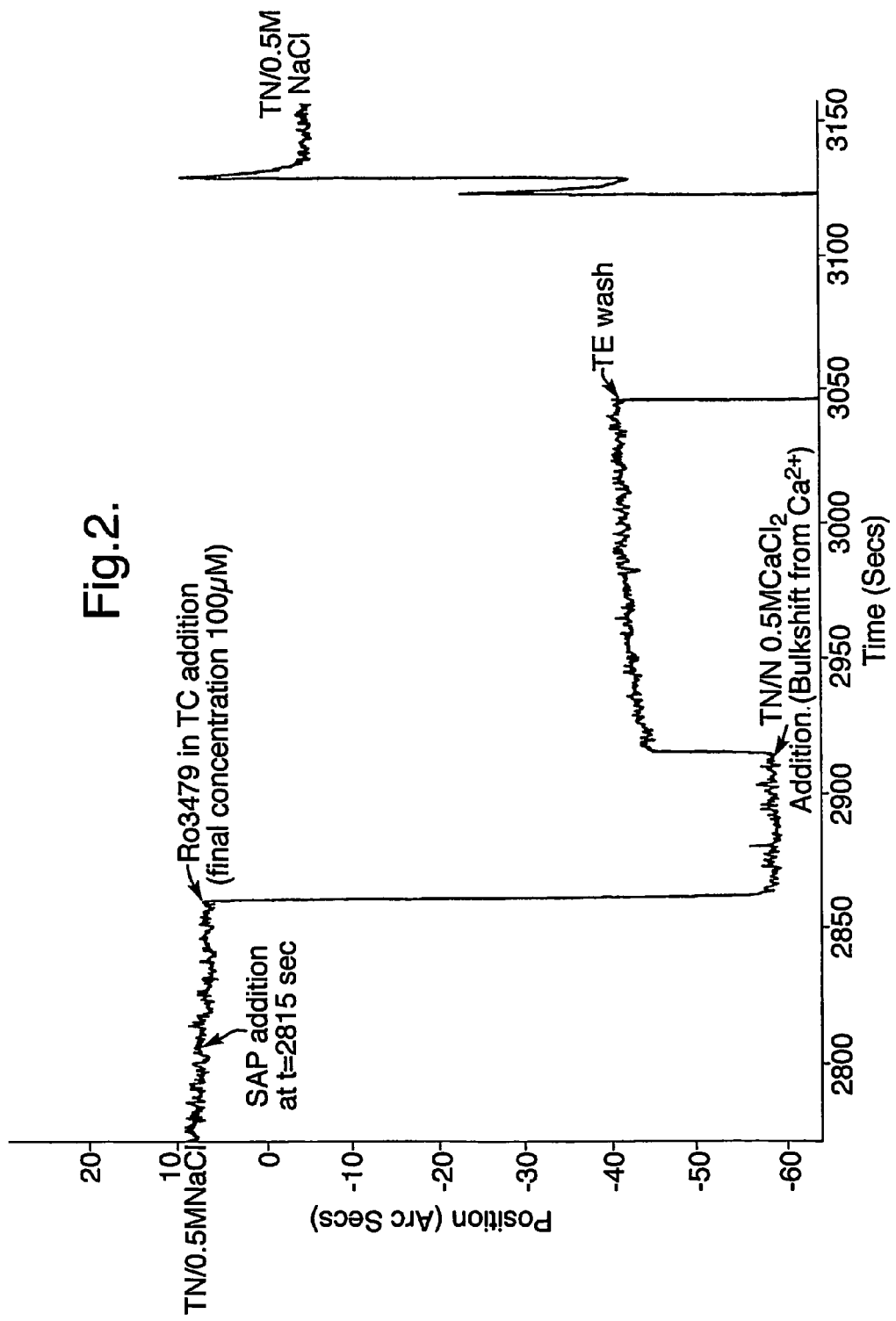
Figure 3:
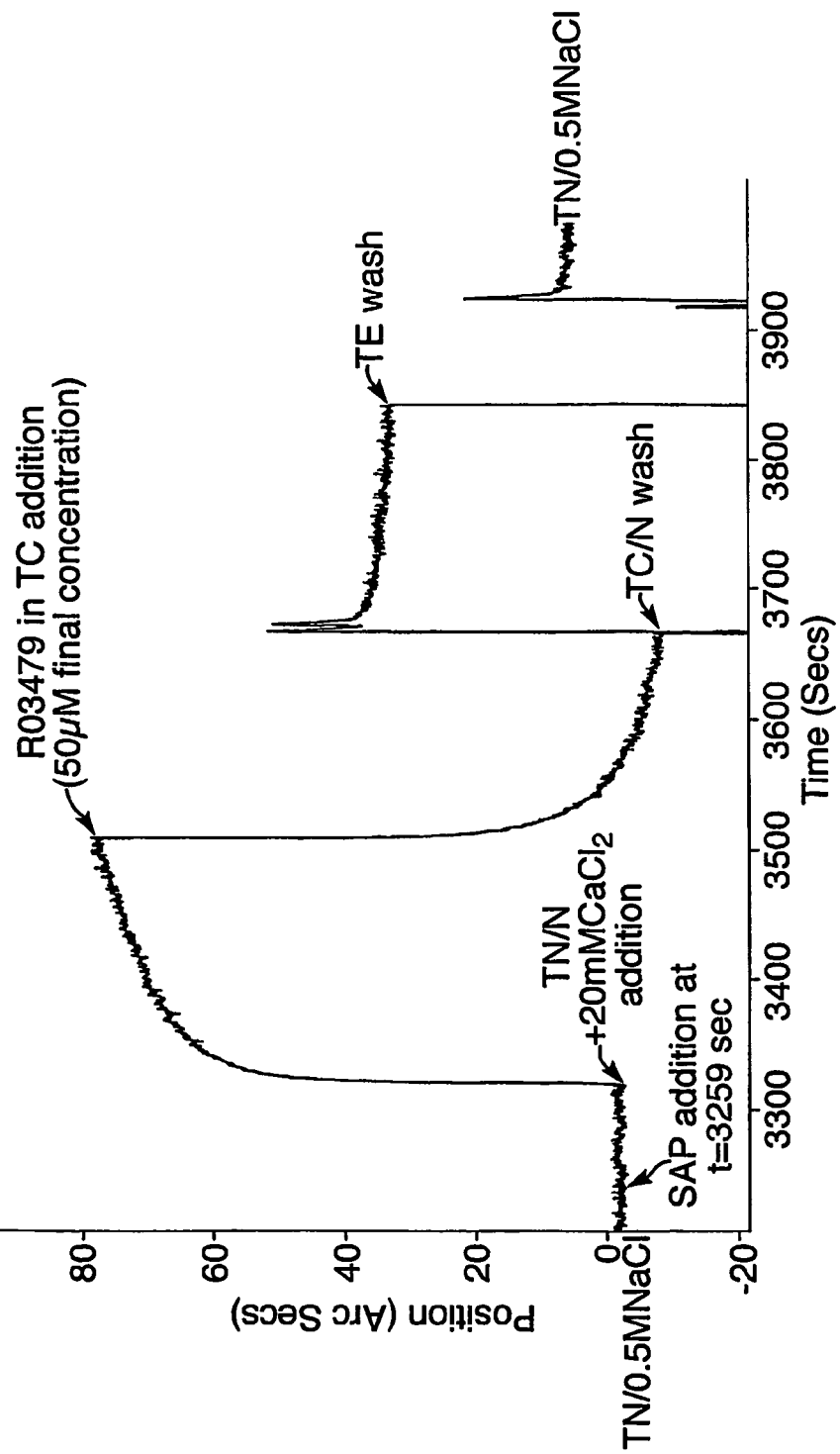

Use of Surface Plasmon Resonance to Detect Inhibition of Calcium Dependent Ligand Binding by SAP Synthetic Aβ-42 amyloid fibrils (28) were covalently immobilised on the reactant surface of the Fisons IAsys surface plasmon resonance instrument, and then exposed to isolated SAP (32) in solution in Tris-buffered physiological saline in the absence of calcium (shown as TN/N in the Figures). No binding of SAP occurred and thus no signal was generated. Introduction of calcium allowed the SAP to bind specifically to the immobilised amyloid fibrils, generating a readily detectable signal (FIG. 1). 1-[(S)-3-Mercapto-2-methylpropionyl]-D-proline (designated on the Figures as Ro-3479) is a specific inhibitor of calcium dependent ligand binding by SAP. Addition of 1-[(S)-3-Mercapto-2-methylpropionyl]-D-proline (Ro-3479) at 500 μmol/l in Tris-buffered physiological saline containing calcium (TC in the Figures), completely reversed the binding of SAP and the corresponding signal (FIG. 1). After addition of SAP in the absence of calcium, followed by Ro-3479 at 100 μmol/l, and then allowing equilibration of the system, subsequent addition of calcium to enable specific calcium dependent ligand binding by SAP was followed by no signal (FIG. 2), indicating that Ro-3479 not only dissociates SAP binding but also inhibits it. The solid phase ligand was regenerated for further calcium dependent ligand binding, by washing it with EDTA in Tris-buffered physiological saline (TE in the Figures), and then re-exposed to SAP in TN buffer followed by calcium. The typical signal reflecting ligand binding by SAP was observed again, and then completely reversed by addition of Ro-3479 at 50 μmol/l (FIG. 3).

Example B

Screening for Inhibitors of Binding of $^{125}$I Radiolabelled SAP to *Neisseria meningitidis* Organisms Immobilized in Microtitre Plates Materials and Methods A suspension of heat killed *Neisseria meningitidis* at 1×10$^8$ organisms per ml in PBS was dispensed to polystyrene microtitre plates at 50 μl volumes per well, and left overnight at 4° C. All wells were then washed three times with 200 μl volumes of PBS containing 0.05% v/v Tween 20, prior to equilibration for 2 min with 0.01M Tris buffered 0.14M NaCl/0.002M CaCl$_2$ at pH 8.0 (TC buffer), containing 4% w/v BSA and 0.05%/v Tween 20 (TCBT buffer). The wells were then emptied before adding to each one the following reagents. For control uninhibited maximal binding: 35 μl TCBT buffer (containing 2.3 mM CaCl$_2$, 5.72% w/v BSA, 0.072% v/v Tween 20), 10 μl TC and 5 μl SAP radiolabelled with $^{125}$I in 0.01M Tris buffered 0.14M NaCl at pH 8.0 (TN buffer), to provide final concentrations of BSA, 4%; Ca$^{2+}$, 2 mM; Tween 20, 0.05%. For background, non-specific, non calcium dependent, binding in the presence of EDTA: 5 μl radiolabelled SAP in TN and 45 μl 0.01M Tris buffered 0.14M NaCl at pH 8.0 containing 11.1 mM EDTA, 4.4% w/v BSA and 0.06% w/v Tween 20 (TEBT buffer) to provide final concentrations of EDTA, 10 mM; BSA, 4%; Tween 20, 0.05%. For testing of inhibitors: 35 μl of TCBT (containing 2.3 mM Ca$^{2+}$, 5.72% BSA and 0.072% Tween 20), 10 μl TC containing test compounds at 10 mM, 1 mM, 100 μM, 10 μM or 1 μM, and 5 μl of radiolabelled SAP in TN. All wells were then incubated at room temperature for 2 h before being washed three times with 200 μl volumes of TCBT, allowed to dry for 1 h at room temperature, and bound radiolabelled SAP was then counted.

The compounds tested in the experiment shown here were a family of molecules developed as inhibitors of SAP binding to amyloid fibrils, following identification of an initial lead molecule during high throughput screening of a large compound library according to U.S. Pat. No. 6,126,918. The original hit was 1-[(S)-3-Mercapto-2-methylpropionyl]-D-proline, (Ro-15-3479), and a dimer of one of its diastereoisomers, (R)-1-[(S)-3-[(S)-3-[(R)-2-carboxy-pyrrolidin-1-yl]-2-methyl-3-oxo-propyldisulfanyl]-2-methyl-propionyl]-pyrrolidine-2-carboxylic acid (Ro-63-3300) was found to be much more potent. The other two diastereoisomers did not inhibit ligand binding by SAP. A chemistry programme then produced, (R)-1-[6-(R)-2-Carboxy-pyrrolidin-1-yl]-6-oxo-hexanoyl]pyrrolidine-2-carboxylic acid (Ro-63-8695) (Example 8b of EP-A-915088) and a family of related molecules, that were tested here. Their chemical names and coded designations are listed below:

Ro-64-4383: (R)-1-[[2,5-Dihydroxy-4-[2-[(R)-2-carboxy-pyrrolidin-1-yl]-2-oxo-ethyl]-phenyl]-acetyl]-pyrrolidine-2-carboxylic acid Ro-642856: (R)-1-[[4-[2-[(R)-2-Carboxy-pyrrolidin-1-yl]-2-oxo-ethoxy]-phenoxy]-acetyl]-pyrrolidine-2-carboxylic acid Ro-63-3300: (R)-1-[(S)-3-[(S)-3-[(R)-2-carboxy-pyrrolidin-1-yl]-2-methyl-3-oxo-propyldisulfanyl]-2-methyl-propionyl]-pyrrolidine-2-carboxylic acid Ro-15-3479: 1-[(S)-3-Mercapto-2-methylpropionyl]-D-proline Ro-64-2848: (R)-1-[[3-[2-[(R)-1-Carboxy-pyrrolidin-1-yl]-2-oxo-ethoxy]-2-methyl-phenoxy]-acetyl]-pyrrolidine-2-carboxylic acid Ro-64-2668: (R)-1-[[3-[2-[(R)-2-Carboxy-pyrrolidin-1-yl]-2-oxo-ethyl]-phenyl]-acetyl]-pyrrolidine-2-carboxylic acid Ro-64-2845: (R)-1-[[2-[2-[(R)-2-carboxy-pyrrolidin-1-yl]-2-oxo-ethoxy]-3-methoxy-phenoxy]-acetyl]-pyrrolidine-2-carboxylic acid Ro-64-2600: (R)-1-[cis-4-[(R)-2-Carboxy-pyrrolidine-1-carbonyl]-cyclohexanecarbonyl]-pyrrolidine-2-carboxylic acid Ro-64-5607: (R)-1-[[4-[2-[(R)-2-Carboxy-pyrrolidin-1-yl]-2-oxo-ethyl]-naphthalen-1-yl]-acetyl]-pyrrolidine-2-carboxylic acid Ro-64-5445: (R)-1-[[5-[2-[(R)-2-Carboxy-pyrrolidin-1-yl]-2-oxo-ethoxy]-naphthalen-1-yloxy]-acetyl]-pyrrolidine-2-carboxylic acid Ro-63-8593: (R)-1-[[2-[2-[(R)-2-Carboxy-pyrrolidin-1-yl]-2-oxo-ethoxy]-phenoxyl]-acetyl]-pyrrolidine-2-carboxylic acid Ro-63-7777: (R)-1-[[4-[2-[(R)-2-Carboxy-pyrrolidin-1-yl]-2-oxo-ethyl]-phenyl]-acetyl]-pyrrolidine-2-carboxylic acid Results The capacity of the compounds tested to inhibit binding of SAP to meningococci is expressed as the percentage by which SAP binding was reduced compared to binding in the absence of any inhibitor (Table 1). All binding was inhibited by EDTA, confirming the specific, calcium dependent, nature of the interaction. Phosphoethanolamine, a well known ligand of SAP (25,32), produced inhibition at high concentration, but only modest effects when diluted. Phosphocholine, the specific ligand of C-reactive protein, the other human plasma pentraxin protein closely related to SAP, had virtually no effect, as expected since there is no other evidence that SAP recognises and binds to phosphocholine under physiological conditions. The Ro-63-8695 family of molecules were potent inhibitors with IC$_{50}$ values in the sub-micromolar range in several cases. These compounds are thus candidates for further testing according to the present invention.

TABLE 1

Percent inhibition by various compounds of binding of radiolabelled SAP to immobilized *Neisseria meningitidis*

| Compound | Molarity | | | | |
|---|---|---|---|---|---|
| | 2 mM | 200 μM | 20 μM | 2 μM | 200 nM |
| None | 0 | 0 | 0 | 0 | 0 |
| EDTA 10 mM | 100 | nd | nd | nd | nd |
| Phosphoethanolamine | 95 | 41 | 32 | 18 | 7 |
| Phosphocholine | 24 | 3 | 4 | 5 | 0 |
| Ro-63-8695 | 100 | 79 | 74 | 61 | 5 |
| Ro-64-4383 | 100 | 100 | 95 | 76 | 1 |
| Ro-64-2856 | 100 | 65 | 74 | 65 | 0 |
| Ro-63-3300 | 100 | 69 | 73 | 68 | 28 |
| Ro-15-3479 | 77 | 54 | 50 | 42 | 3 |
| Ro-64-2848 | 100 | 100 | 93 | 64 | 1 |
| Ro-64-2668 | 100 | 100 | 92 | 64 | 28 |
| Ro-64-2845 | 100 | 93 | 92 | 74 | 19 |
| Ro-64-2600 | 100 | 100 | 93 | 73 | 31 |
| Ro-64-5607 | 100 | 100 | 89 | 69 | 13 |
| Ro-64-5445 | 100 | 100 | 81 | 72 | 30 |
| Ro-63-8593 | 100 | 100 | 87 | 77 | 18 |
| Ro-63-7777 | 100 | 100 | 73 | 64 | 7 |

Example C

Screening for Inhibitors of Binding of $^{125}$I Radiolabeled SAP to Chromatin Immobilized in Microtitre Plates Materials and Methods A solution containing 100 μg/ml chicken erythrocyte native long chromatin (27), in PBS adjusted to pH 9, was dispensed to microtitre plates containing N-oxysuccinimide-activated surfaces, at 50 μl volumes per well and left at room temperature for 1 h. All wells were then washed three times with 200 μl volumes of PBS, pH 7.4, containing 0.05% v/v Tween 20 (PBST) and unreacted active sites were blocked by the addition of 50 μl of 2% w/v BSA in PBS, pH 7.4, to each well, for 30 min at room temperature. Wells were then washed three times with 200 μl volumes of PBST prior to equilibration for 2 min with 0.01M Tris buffered 0.14M NaCl/0.002M CaCl$_2$ at pH 8.0 (TC buffer), containing 4% w/v BSA and 0.05% v/v Tween 20 (TCBT buffer). The wells were then emptied before adding to each one the following reagents. For control uninhibited maximal binding: 35 μl TCBT buffer (containing 2.3 mM CaCl$_2$, 5.72% w/v BSA, 0.072% v/v Tween 20), 10 μl TC and 5 μl SAP radiolabelled with $^{125}$I-in 0.01M Tris buffered 0.14M NaCl at pH 8.0 (TN buffer), to provide final concentrations of BSA, 4%; Ca$^{2+}$, 2 mM; Tween 20, 0.05%. For background, non specific, non calcium dependent, binding in the presence of EDTA: 5 μl radiolabelled SAP in TN and 45 μl 0.01M Tris buffered 0.14M NaCl at pH 8.0 containing 11.1 mM EDTA, 4.4% w/v BSA and 0.06% w/v Tween 20 (TEBT buffer) to provide final concentrations of EDTA, 10 mM; BSA, 4%; Tween 20, 0.05%. For testing of inhibitors: 35 μl of TCBT (containing 2.3 mM Ca$^{2+}$, 5.72% BSA and 0.072% Tween 20), 10 μl TC containing test compounds at 10 mM, 1 mM, 100 μM, 10 μM or 1 μM, and 5 μl of radiolabelled SAP in TN. All wells were then incubated at room temperature for 2 h before being washed three times with 200 μl volumes of TCBT, allowed to dry for 1 h at room temperature, and bound radiolabelled SAP was then counted. The compounds tested in the experiment shown here were the same as those specified in Example B above.

Results

The capacity of the compounds tested to inhibit binding of SAP to chromatin is expressed as the percentage by which SAP binding was reduced compared to binding in the absence of any inhibitor (Table 2). All binding was inhibited by EDTA, confirming the specific, calcium dependent, nature of the interaction. Binding to control wells without chromatin and just blocked with BSA was at the same background level as seen with complete inhibition by EDTA or the specific inhibitors. Phosphoethanolamine, a well known ligand of SAP (25,32), produced inhibition at high concentration, but only modest effects when diluted. Phosphocholine, the specific ligand of C-reactive protein, the other human plasma pentraxin protein closely related to SAP, had virtually no effect, as expected since there is no other evidence that SAP recognises and binds to phosphocholine under physiological conditions. The Ro-63-8695 family of molecules were potent inhibitors with IC$_{50}$ values in the micromolar range in several cases. These compounds are thus candidates for further testing according to the present invention, although interestingly this assay was less sensitive than that using meningococci as the immobilised ligand.

TABLE 2

Percent inhibition by various compounds of binding of radiolabelled SAP to immobilized native long chromatin

| Compound | Molarity | | | | |
|---|---|---|---|---|---|
| | 2 mM | 200 μM | 20 μM | 2 μM | 200 nM |
| None | 0 | 0 | 0 | 0 | 0 |
| Phosphoethanolamine | 94 | 59 | 36 | 9 | 3 |
| Phosphocholine | 19 | 3 | 0 | 0 | 2 |
| Ro-63-8695 | 93 | 87 | 69 | 29 | 1 |
| Ro-64-4383 | 97 | 88 | 78 | 45 | 0 |
| Ro-64-2856 | 91 | 75 | 56 | 36 | 1 |
| Ro-63-3300 | 99 | 88 | 69 | 34 | 3 |
| Ro-15-3479 | 81 | 46 | 72 | 14 | 0 |
| Ro-64-2848 | 98 | 95 | 65 | 22 | 0 |
| Ro-64-2668 | 98 | 94 | 56 | 18 | 0 |
| Ro-64-2845 | 100 | 96 | 75 | Nd | 11 |

TABLE 2-continued

Percent inhibition by various compounds of binding of radiolabelled SAP to immobilized native long chromatin

| Compound | Molarity | | | | |
|---|---|---|---|---|---|
| | 2 mM | 200 μM | 20 μM | 2 μM | 200 nM |
| Ro-64-2600 | 100 | 94 | 67 | 35 | 1 |
| Ro-64-5607 | 100 | 96 | 77 | 35 | 15 |
| Ro-64-5445 | 96 | 82 | 74 | 51 | 12 |
| Ro-63-8593 | 96 | 89 | 77 | 34 | 7 |
| Ro-63-7777 | 92 | 66 | 39 | 19 | 4 |

Example D

Screening for Inhibitors of Binding of $^{125}$I Radiolabelled SAP to Influenza Virus Immobilized in Microtitre Plates Materials and Methods A concentrated suspension of purified influenza virus A/Shanghai/24/90 at 10 mg protein per ml in PBS was diluted 1:50 in PBS and then dispensed to polystyrene microtitre plates at 50 μl volumes per well, and left overnight at 4° C. All wells were then emptied before blocking by addition to each well of 200 μl of 2% w/v BSA in PBS and incubation at room temperature for 1 h. All wells were then washed three times with 200 μl volumes of PBS containing 0.05% v/v Tween 20, prior to equilibration for 2 min with 0.01M Tris buffered 0.14M NaCl/0.002M CaCl$_2$ at pH 8.0 (TC buffer), containing 4% w/v BSA and 0.05% v/v Tween 20 (TCBT buffer). The wells were then emptied before adding to each one the following reagents. For control uninhibited maximal binding: 35 μl TCBT buffer (containing 2.3 mM CaCl$_2$, 5.72% w/v BSA, 0.072% v/v Tween 20), 10 μl TC and 5 μl SAP radiolabelled with $^{125}$I (32) in 0.01M Tris buffered 0.14M NaCl at pH 8.0 (TN buffer), to provide final concentrations of BSA, 4%; Ca$^{2+}$, 2 mM; Tween 20, 0.05%. For background, non-specific, non calcium dependent, binding in the presence of EDTA: 5 μl radiolabelled SAP in TN and 45 μl 0.01M Tris buffered 0.14M NaCl at pH 8.0 containing 11.1 mM EDTA, 4.4% w/v BSA and 0.06% w/v Tween 20 (TEBT buffer) to provide final concentrations of EDTA, 10 mM; BSA, 4%; Tween 20, 0.05%. For testing of inhibitors: 35 μl of TCBT (containing 2.3 mM Ca$^{2+}$, 5.72% BSA and 0.072% Tween 20), 10 μl TC containing test compounds at 10 mM, 1 mM, 100 μM, 10 μM or 1 μM, and 5 μl of radiolabelled SAP in TN. All wells were then incubated at room temperature for 2 h before being washed three times with 200 μl volumes of TCBT, allowed to dry for 1 h at room temperature, and bound radiolabelled SAP was then counted. The compounds tested in the experiment shown here were the same as those specified in Example B above.

Results

The capacity of the compounds tested to inhibit binding of SAP to the immobilised influenza virus is expressed as the percentage by which SAP binding was reduced compared to binding in the absence of any inhibitor (Table 3). All binding was inhibited by EDTA, confirming the specific, calcium dependent, nature of the interaction. Binding to control wells without virus and just blocked with BSA was at the same background level as seen with complete inhibition by EDTA or the specific inhibitors. Phosphoethanolamine, a well known ligand of SAP (25,32), produced inhibition at high concentration, but only modest effects when diluted. Phosphocholine, the specific ligand of C-reactive protein, the other human plasma pentraxin protein closely related to SAP, had virtually no effect, as expected since there is no other evidence that SAP recognises and binds to phosphocholine under physiological conditions. The Ro-63-8695 family of molecules were potent inhibitors with $IC_{50}$ values in the sub-micromolar, high nanomolar, range in several cases. These compounds are thus candidates for further testing according to the present invention, and interestingly this assay was more sensitive than those using either whole meningococci or native long chromatin as the immobilised ligand.

TABLE 3

Percent inhibition by various compounds of binding of radiolabelled SAP to immobilized influenza virus

| Compound | Molarity | | | | |
|---|---|---|---|---|---|
| | 2 mM | 200 µM | 20 µM | 2 µM | 200 nM |
| None | 0 | 0 | 0 | 0 | 0 |
| Phosphoethanolamine | 69 | 51 | 42 | 8 | 1 |
| Phosphocholine | 3 | 5 | 5 | 2 | 0 |
| Ro-63-8695 | 98 | 96 | 90 | 81 | 36 |
| Ro-64-4383 | 89 | 89 | 80 | 57 | 24 |
| Ro-64-2856 | 87 | 84 | 82 | 77 | 3 |
| Ro-63-3300 | 91 | 91 | 90 | 78 | 47 |
| Ro-15-3479 | 68 | 51 | 40 | 30 | 12 |
| Ro-64-2848 | 85 | 81 | 81 | 65 | 24 |
| Ro-64-2668 | 82 | 77 | 73 | 68 | 25 |
| Ro-64-2845 | 89 | 77 | 62 | 52 | 16 |
| Ro-64-2600 | 92 | 89 | 83 | 76 | 0 |
| Ro-64-5607 | 98 | 94 | 95 | 64 | 4 |
| Ro-64-5445 | 80 | 76 | 64 | 51 | 23 |
| Ro-63-8593 | 94 | 93 | 88 | 68 | 44 |
| Ro-63-7777 | 89 | 89 | 85 | 65 | 37 |

Example E

Accumulation of Labelled SAP in Joints of Patients Suffering from Arthritis

Accumulation of labelled SAP was found in joints of patients without dialysis amyloidosis who were suffering from other forms of arthritis: 5 individuals with osteoarthritis (FIG. 4), 12 with rheumatoid arthritis, and one subject with a traumatic effusion. In each of these patients, labelled SAP was detected in all joints with a significant effusion, regardless of aetiology. This in itself is not surprising since it is known that plasma proteins enter joint effusions. However, in 20 out of 30 patients with various different arthropathies we have also observed uptake of labelled SAP into some joints that did not have clinically detectable effusions.

Figure 4:
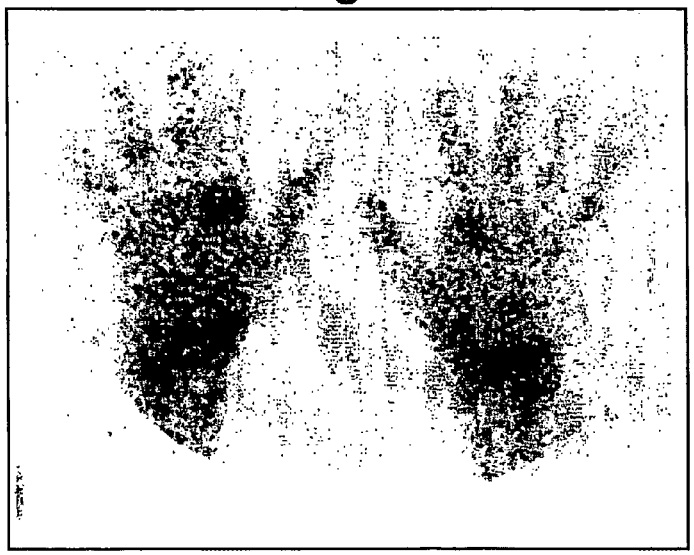
FIG. 4 shows a scintigraphic image of the hands of a patient with osteoarthritis 24 hours after intravenous injection of $^{123}$I-labelled SAP.

FIG. 4 shows a scintigraphic image of the hands of a patient with osteoarthritis 24 h after intravenous injection of $^{123}$I-labelled SAP. Uptake and retention of SAP is indicated in both carpal areas, in the second metacarpophalangeal joints, and some interphalangeal joints.

One possible mechanism for localisation of SAP from the blood to a diseased joint may be the presence within the joint of amyloid deposits in articular and peri-articular structures. There is indeed extensive evidence for the widespread presence of microscopic amyloid deposits in the synovium, articular cartilage and/or joint capsules of elderly individuals (33-44). However the overall impression from these observational studies of autopsy and/or resection specimens is that the amyloid deposits are mainly associated with increasing age of the subjects and not particularly with extent or severity of clinical or pathological manifestations of osteoarthritis. Alternatively, or in addition, SAP may be binding to ligands on structures other than amyloid fibrils that are present in inflamed or damaged joints. The calcium-dependent binding of SAP to glycosaminoglycans in vitro has been reported (45), but was specific for heparan and dermatan sulphates, rather than the chrondroitin sulphate and hyaluronic acid that are most abundant in cartilage and synovial fluid respectively. Nevertheless, glycosaminoglycans are ubiquitous in connective tissue and may be abnormally exposed and thereby provide ligands for SAP in and around diseased joints. Another ligand to which SAP binds avidly, in vivo as well as in vitro, is DNA (26,27), both free and within chromatin when this is exposed by cell death (46), and SAP also binds to apoptotic cells in vivo (47). Increased cell death in inflamed joints, whether by apoptosis or by necrosis, exposing chromatin, may provide an abnormal density of ligands and thus a focus for SAP deposition.

Example F

SAP Binding to Ligands in Diseased Joints

Figure 5:
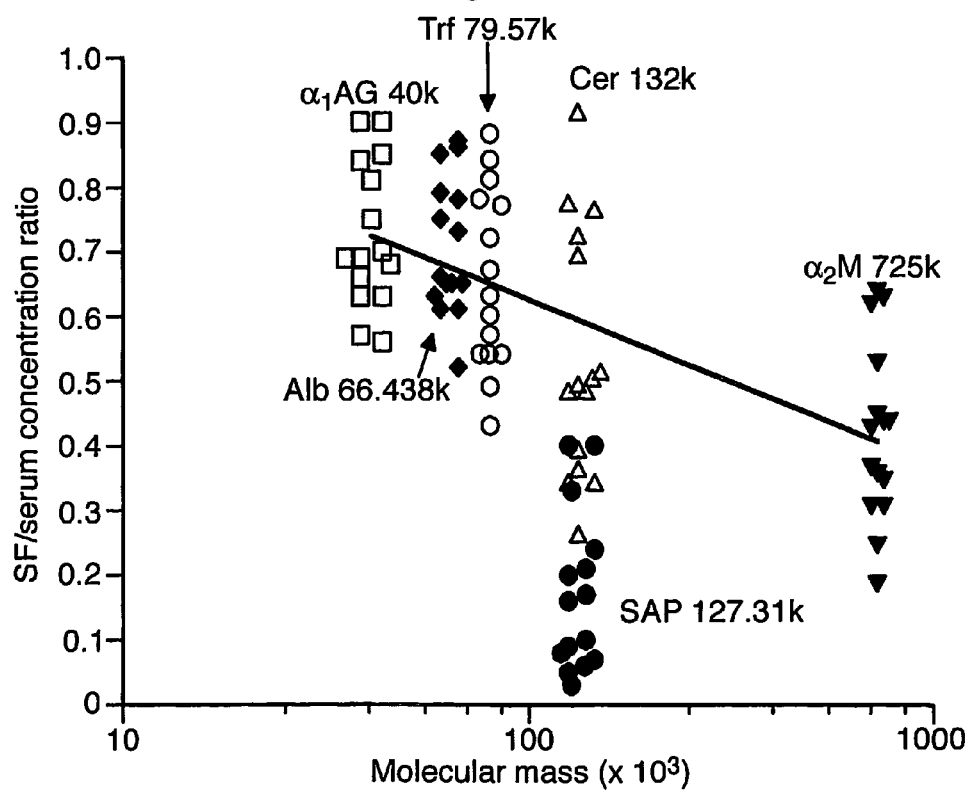
FIG. 5 shows the ratio of the concentration of the various proteins in the synovial fluid and serum from patients with various forms of arthritis-causing effusions.

In order to test whether SAP may be binding to ligands in diseased joints, we first compared the distribution of radiolabelled human serum albumin with that of SAP in two patients. In one with proven dialysis associated amyloid, the joint uptake of SAP was very much greater than that of albumin, showing that the SAP localisation was specific for amyloid. In contrast, in a patient with active rheumatoid arthritis and multiple affected joints with effusions, the localisation of albumin and SAP were generally comparable, suggesting a similar non-specific process of effusion into the synovial space for both proteins, although occasional joints showed greater retention of SAP than of albumin. Furthermore, in one patient whose knee joint effusions were aspirated to dryness 24 h after injection of radiolabelled SAP, there remained strong localisation of SAP in the joints. Secondly, we measured the synovial fluid and serum concentrations of SAP and other plasma proteins in paired samples from 15 patients with joint effusions of different aetiologies, and calculated the synovial fluid:serum ratios. There is a well known inverse linear relationship between this ratio and the relative molecular mass of the proteins, reflecting their relative ease of access by diffusion from the circulation into the joint space. However, the ratio was remarkably and substantially lower for SAP than expected for a protein of its molecular mass (FIG. 5). This indicates that SAP, which evidently can gain access to the synovial fluid, as shown by our studies with labelled SAP, is probably binding to structure(s) within the joint and is therefore not available for detection and assay in the synovial fluid itself.

FIG. 5 shows the ratio of the concentration of various plasma proteins in the synovial fluid and serum from patients with various forms of arthritis causing effusions. There is a linear relationship, r=0.62, between the relative molecular mass and the synovial fluid/serum concentration ratio for all the proteins shown here except SAP, for which the synovial fluid concentration is markedly lower than predicted from its molecular mass and serum concentration. (Key: $\alpha_1$AG, $\alpha_1$-acid glycoprotein; Alb, albumin; Trf, transferrin; Cer, ceruloplasmin; $\alpha_2$M, $\alpha_2$-macroglobulin.)

The very common and widespread microscopic amyloid deposits in aged and osteoarthritic joints have not hitherto been thought to contribute to the pathogenesis or symptoms of osteoarthritis. It is also not clear how binding of SAP to either amyloid fibrils or other structures in joints might be pathogenetic in osteoarthritis. Although artificially aggregated SAP can activate the complement system (48), and could thereby be pro-inflammatory, the binding of SAP to any of its known ligands not only does not activate complement, but actually inhibits complement activation by the substrate itself (49,50). Also, there is no evidence for complement activation either locally or systemically in patients with osteoarthritis. Nevertheless, in the light of our observations of SAP localisation to joints and the unexpectedly low concentration of SAP free in synovial fluid, we tested whether SAP might be involved in osteoarthritis.

Example G

Treatment of Patients with Osteoarthritis

Two examples demonstrate the efficacy of such treatment.

1) RJ, a 64 year old retired General Practitioner living in New Zealand, has a long history of bone and joint injuries, starting as a child on a farm and continuing as a teenager and then adult playing rugby and skiing. From the age of 42 he has suffered from pain and swelling of previously damaged joints following manual work and especially in cold weather. The proximal interphalangeal joints of the left middle and right fourth fingers, the right elbow and the mid-thoracic intervertebral joints have been most affected. Symptoms and signs have progressively worsened over the past 22 years, so that his capacity for physical work had become very restricted and during winter he has required frequent or continuous treatment with non-steroidal anti-inflammatory drugs. These are all typical manifestations of osteoarthritis. In 2000 the discovery of impaired renal function led eventually to a second, and completely separate diagnosis of hereditary systemic amyloidosis caused by a mutation in the gene for fibrinogen A α-chain. This type of amyloidosis does not affect the joints and its pathogenesis and clinical manifestations are completely unrelated to osteoarthritis.

He started experimental treatment for his amyloidosis on 9 Oct. 2001 with (R)-1-[6-[(R)-2-Carboxy-pyrrolidin-1-yl]-6-oxo-hexanoyl]pyrrolidine-2-carboxylic acid, 10 mg b.d. by subcutaneous injection. In January 2002, after three months on this potent SAP depleting drug and with his plasma SAP concentration consistently reduced by over 95%, he first noted that his symptoms of arthritis were less troublesome than before. This improvement was sustained and increased so that by April 2002, the autumn in New Zealand, it was impressively beyond doubt. Throughout that winter, for the first time in many years, he no longer required treatment with non-steroidal anti-inflammatory drugs, despite increased physical activity. He has continued treatment with (R)-1-[6-[(R)-2-Carboxy-pyrrolidin-1-yl]-6-oxo-hexanoyl]pyrrolidine-2-carboxylic acid up to the present (June 2003) and all his symptoms of osteoarthritis have, remarkably, remained in remission. Over the past few months he has been doing regular hard physical work on the land, fencing and landscaping, including lifting and carrying significant weights, without suffering any of the pain and swelling that previously severely affected him even without the stress of unusual physical activity.

2) CD, a 49 year old service worker from Wales, had a 6-8 year history of pain and reduced function in several joints. Her shoulders were painful, particularly when reaching up or behind her head, making drying her hair and some household tasks painful and difficult. She had mid-thoracic back pain and bilateral ankle aches on most days, usually caused by prolonged standing. She also experienced pain in her right wrist when performing some tasks, particularly opening jars, a manoeuvre that she found difficult. These symptoms are all compatible with osteoarthritis.

CD has hereditary systemic amyloidosis caused by a mutation in the gene for apolipoprotein AI, diagnosed in October 2001 during investigation of chronic renal impairment. This type of amyloidosis does not affect the joints or cause arthritic symptoms. She started experimental treatment for her amyloidosis on 22 Oct. 2001 with (R)-1-[6-[(R)-2-Carboxy-pyrrolidin-1-yl]-6-oxo-hexanoyl]pyrrolidine-2-carboxylic acid, 15 mg b.d. by subcutaneous injection. In December 2001, after two months on this potent SAP depleting drug and with her plasma SAP concentration consistently reduced by over 95%, she first noted that her joint symptoms were significantly less troublesome than before. This improvement was sustained and increased so that by January 2002 she was free of pain and had normal function of her joints. Treatment with (R)-1-[6-[(R)-2-Carboxy-pyrrolidin-1-yl]-6-oxo-hexanoyl] pyrrolidine-2-carboxylic acid finished in October 2002 and her remarkable remission has continued to the present (June 2003).

REFERENCES

1. Brion, P. H. and Kalunian, K. C. (2003) Osteoarthritis. In: Oxford Textbook of Medicine, 4th Ed., Vol. 3 (Warrell, D. A., Cox, T. M., Firth, J. D. and Benz, E. J., Jr., eds.), Oxford University Press, Oxford, pp. 62-68.
2. Osmand, A. P., Friedenson, B., Gewurz, H., Painter, R. H., Hofmann, T. and Shelton, E. (1977) Characterisation of C-reactive protein and the complement subcomponent Clt as homologous proteins displaying cyclic pentameric symmetry (pentraxins). Proc. Natl. Acad. Sci. USA, 74: 739-743.
3. Pepys, M. B. and Baltz, M. L. (1983) Acute phase proteins with special reference to C-reactive protein and related proteins (pentaxins) and serum amyloid A protein. Adv. Immunol., 34: 141-212.
4. Srinivasan, N., White, H. E., Emsley, J., Wood, S. P., Pepys, M. B. and Blundell, T. L. (1994) Comparative analyses of pentraxins: implications for protomer assembly and ligand binding. Structure, 2: 1017-1027.
5. Srinivasan, N., Rufino, S. D., Pepys, M. B., Wood, S. P. and Blundell, T. L. (1996) A superfamily of proteins with the lectin fold. Chemtracts-Biochem. Mol. Biol., 6: 149-164.
6. Baltz, M. L., de Beer, F. C., Feinstein, A., Munn, E. A., Milstein, C. P., Fletcher, T. C., March, J. F., Taylor, J., Bruton, C., Clamp, J. R., Davies, A. J. S, and Pepys, M. B. (1982) Phylogenetic aspects of C-reactive protein and related proteins. Ann. N.Y. Acad. Sci., 389: 49-75.
7. Tennent, G. A., Butler, P. J. G., Hutton, T., Woolfit, A. R., Harvey, D. J., Rademacher, T. W. and Pepys, M. B. (1993) Molecular characterization of Limulus polyphemus C-reactive protein. I. Subunit composition Eur. J. Biochem., 214: 91-97.
8. Pepys, M. B., Rademacher, T. W., Amatayakul-Chantler, S., Williams, P., Noble, G. E., Hutchinson, W. L., Hawkins, P. N., Nelson, S. R., Gallimore, J. R., Herbert, J., Hutton, T. and Dwek, R. A. (1994) Human serum amyloid P component is an invariant constituent of amyloid deposits and has a uniquely homogeneous glycostructure. Proc. Natl. Acad. Sci. USA, 91: 5602-5606.
9. Pepys, M. B., Booth, D. R., Hutchinson, W. L., Gallimore, J. R., Collins, P. M. and Hohenester, E. (1997) Amyloid P component. A critical review. Amyloid: Int. J. Exp. Clin. Invest., 4: 274-295.
10. Sunde, M., Serpell, L. C., Bartlam, M., Fraser, P. E., Pepys, M. B. and Blake, C. C. F. (1997) Common core structure of amyloid fibrils by synchrotron X-ray diffraction. *J. Mol. Biol.*, 273: 729-739.

11. Nelson, S. R., Lyon, M., Gallagher, J. T., Johnson, E. A. and Pepys, M. B. (1991) Isolation and characterization of the integral glycosaminoglycan constituents of human amyloid A and monoclonal light-chain amyloid fibrils. *Biochem. J.*, 275: 67-73.

12. Pepys, M. B., Dyck, R. F., de Beer, F. C., Skinner, M. and Cohen, A. S. (1979) Binding of serum amyloid P component (SAP) by amyloid fibrils. *Clin. Exp. Immunol.*, 38: 284-293.

13. Caspi, D., Zalzman, S., Baratz, M., Teitelbaum, Z., Yaron, M., Pras, M., Baltz, M. L. and Pepys, M. B. (1987) Imaging of experimental amyloidosis with $^{131}$I-serum amyloid P component. *Arthritis Rheum.*, 30: 1303-1306.

14. Hawkins, P. N., Myers, M. J., Epenetos, A. A., Caspi, D. and Pepys, M. B. (1988) Specific localization and imaging of amyloid deposits in vivo using $^{123}$I-labeled serum amyloid P component. *J. Exp. Med.*, 167: 903-913.

15. Hawkins, P. N., Lavender, J. P. and Pepys, M. B. (1990) Evaluation of systemic amyloidosis by scintigraphy with $^{123}$I-labeled serum amyloid P component. *N. Engl. J. Med.*, 323: 508-513.

16. Nelson, S. R., Hawkins, P. N., Richardson, S., Lavender, J. P., Sethi, D., Gower, P. E., Pugh, C. W., Winearls, C. G., Oliver, D. O. and Pepys, M. B. (1991) Imaging of haemodialysis-associated amyloidosis with $^{123}$I-serum amyloid P component. *Lancet*, 338: 335-339.

17. Tan, S. Y., Baillod, R., Brown, E., Farrington, K., Soper, C., Percy, M., Clutterbuck, E., Madhoo, S., Pepys, M. B. and Hawkins, P. N. (1999) Clinical, radiological and serum amyloid P component scintigraphic features of $\beta_2$-microglobulin amyloidosis associated with continuous ambulatory peritoneal dialysis. *Nephrol. Dial. Transplant.*, 14: 1467-1471.

18. Baltz, M. L., de Beer, F. C., Feinstein, A. and Pepys, M. B. (1982) Calcium-dependent aggregation of human serum amyloid P component. *Biochim. Biophys. Acta*, 701: 229-236.

19. Hutchinson, W. L., Hohenester, E. and Pepys, M. B. (2000) Human serum amyloid P component is a single uncomplexed pentamer in whole serum. *Mol. Med.*, 6: 482-493.

20. Hind, C. R. K., Collins, P. M., Baltz, M. L. and Pepys, M. B. (1985) Human serum amyloid P component, a circulating lectin with specificity for the cyclic 4,6-pyruvate acetal of galactose. Interactions with various bacteria *Biochem. J.*, 225:107-111.

21. Noursadeghi, M., Bickerstaff, M. C. M., Gallimore, J. R., Herbert, J., Cohen, J. and Pepys, M. B. (2000) Role of serum amyloid P component in bacterial infection: protection of the host or protection of the pathogen. *Proc. Natl. Acad. Sci. USA*, 97: 14584-14589.

22. Andersen, O., Vilsgaard Ravn, K, Sorensen, I. J., Jonson, G., Holm Nielsen, E. and Svehag, S.-E. (1997) Serum amyloid P component binds to influenza A virus haemagglutinin and inhibits the virus infection in vitro. *Scand. J. Immunol.*, 46: 331-337.

23. Pepys, M. B., Herbert, J., Hutchinson, W. L., Tennent, G. A., Lachmann, H. J., Gallimore, J. R., Lovat, L. B., Bartfai, T., Alanine, A., Hertel, C., Hoffmann, T., Jakob-Roetne, R., Norcross, R. D., Kemp, J. A., Yamamura, K., Suzuki, M., Taylor, G. W., Murray, S., Thompson, D., Purvis, A., Kolstoe, S., Wood, S. P. and Hawkins, P. N. (2002) Targeted pharmacological depletion of serum amyloid P component for treatment of human amyloidosis. *Nature*, 417: 254-259.

24. Pepys, M. B., Dash, A. C., Munn, E. A., Feinstein, A., Skinner, M., Cohen, A. S., Gewurz, H., Osmand, A. P. and Painter, R. H. (1977) Isolation of amyloid P component (protein AP) from normal serum as a calcium-dependent binding protein. *Lancet*, i: 1029-1031.

25. Pontet, M., Engler, R. and Jayle, M. F. (1978) One step preparation of both human C-reactive protein and C1t. *Fed. Eur. Biol. Soc. Lett.*, 88: 172-175.

26. Pepys, M. B. and Butler, P. J. G. (1987) Serum amyloid P component is the major calcium-dependent specific DNA binding protein of the serum. *Biochem. Biophys. Res. Commun.*, 148: 308-313.

27. Butler, P. J. G., Tennent, G. A. and Pepys, M. B. (1990) Pentraxin-chromatin interactions: serum amyloid P component specifically displaces H1-type histones and solubilizes native long chromatin. *J. Exp. Med.*, 172: 13-18.

28. Tennent, G. A., Lovat, L. B. and Pepys, M. B. (1995) Serum amyloid P component prevents proteolysis of the amyloid fibrils of Alzheimer's disease and systemic amyloidosis. *Proc. Natl. Acad. Sci. USA*, 92: 4299-4303.

29. de Beer, F. C., Baltz, M., Holford, S., Feinstein, A. and Pepys, M. B. (1981) Fibronectin and C4-binding protein are selectively bound by aggregated amyloid P component. *J. Exp. Med.*, 154: 1134-1149.

30. Baltz, M. L., Dyck, R. F. and Pepys, M. B. (1985) Studies of the in vivo synthesis and catabolism of serum amyloid P component (SAP) in the mouse. *Clin. Exp. Immunol.*, 59: 235-242.

31. Hawkins, P. N., Wootton, R. and Pepys, M. B. (1990) Metabolic studies of radioiodinated serum amyloid P component in normal subjects and patients with systemic amyloidosis. *J. Clin. Invest.*, 86: 1862-1869.

32. Hawkins, P. N., Tennent, G. A., Woo, P: and Pepys, M. B. (1991) Studies in vivo and in vitro of serum amyloid P component in normals and in a patient with AA amyloidosis. *Clin. Exp. Immunol.*, 84: 308-316.

33. Goffin, Y. A., Thoua, Y. and Potvliege, P. R. (1981) Microdeposition of amyloid in the joints. *Ann. Rheum. Dis.*, 40: 27-33.

34. Sorensen, K. H., Stubbe Teglbjaerg, P., Ladefoged, C. and Christensen, H. E. (1981) Pyrophosphate arthritis with local amyloid deposition. *Acta Orthop. Scand.*, 52: 129-133.

35. Egan, M. S., Goldenberg, D. L., Cohen, A. S. and Segal, D. (1982) The association of amyloid deposits and osteoarthritis. *Arthritis Rheum.*, 25: 204-208.

36. Ladefoged, C. (1982) Amyloid deposits in human hip joints. A macroscopic, light and polarization microscopic and electron microscopic study of congophilic substance with green dichroism in hip joints. *Acta Path. Microbiol. Immunol. Scand. Sect.*, 90: 5-10.

37. Ladefoged, C., Christensen, H. E. and Sørensen, K. H. (1982) Amyloid in osteoarthritic hip joints. Deposition in cartilage and capsule. Semiquantitative aspects. *Acta Orthop. Scand.*, 53: 587-590.

38. Ladefoged, C. (1983) Amyloid in osteoarthritic hip joints: deposits in relation to chondromatosis, pyrophosphate, and inflammatory cell infiltrate in the synovial membrane and fibrous capsule. *Ann. Rheum. Dis.*, 42: 659-664.

39. Takeda, T., Sanada, H., Ishii, M., Matsushita, M., Yamamuro, T., Shimizu, K. and Hosokawa, M. (1984) Age-associated amyloid deposition in surgically-removed herniated intervertebral discs. *Arthritis Rheum.*, 27: 1063-1065.

40. Bartley, C. J., Orford, C. R. and Gardner, D. L. (1985) Amyloid in ageing articular cartilage. *J. Pathol.*, 145: 107A.

41. Cary, N. R. B. (1985) Clinicopathological importance of deposits of amyloid in the femoral head. *J. Clin. Pathol.*, 38: 868-872.
42. Mitrovic, D. R., Stankovic, A., Quintero, M. and Ryckewaert, A. (1985) Amyloid deposits in human knee and hip joints. *Rheumatol. Int.*, 5: 83-89.
43. Ladefoged, C. (1986) Amyloid deposits in the knee joint at autopsy. *Ann. Rheum. Dis.*, 45: 668-672.
44. Lakhanpal, S., Li, C. Y., Gertz, M. A., Kyle, R. A. and Hunder, G. G. (1987) Synovial fluid analysis for diagnosis of amyloid arthropathy. *Arthritis Rheum.*, 30: 419-423.
45. Hamazaki, H. (1987) $Ca^{2+}$-mediated association of human serum amyloid P component with heparan sulfate and dermatan sulfate. *J. Biol. Chem.*, 262: 1456-1460.
46. Breathnach, S. M., Kofler, H., Sepp, N., Ashworth, J., Woodrow, D., Pepys, M. B. and Hintner, H. (1989) Serum amyloid P component binds to cell nuclei in vitro and to in vivo deposits of extracellular chromatin in systemic lupus erythematosus. *J. Exp. Med.*, 170: 1433-1438.
47. Hintner, H., Booker, J., Ashworth, J., Auböck, J., Pepys, M. B. and Breathnach, S. M. (1988) Amyloid P component binds to keratin bodies in human skin and to isolated keratin filament aggregates in vitro. *J. Invest. Dermatol.*, 91: 22-28.
48. Ying, S.-C., Gewurz, A. T., Jiang, H. and Gewurz, H. (1993) Human serum amyloid P component oligomers bind and activate the classical complement pathway via residues 14-26 and 76-92 of the A chain collagen-like region of C1q. *J. Immunol.*, 150: 169-176.
49. Butler, P. J. G. (1983) The folding of chromatin. *CRC Crit. Rev. Biochem.*, 15: 57-91.
50. de Haas, C. J. C., van Leeuwen, E. M. M., van Bommel, T., Verhoef, J., van Kessel, K. P. M. and van Strijp, J. A. G. (2000) Serum amyloid P component bound to gram-negative bacteria prevents lipopolysaccharide-mediated classical pathway complement activation. *Infect. Immun.*, 68: 1753-1759.

The invention claimed is:

1. A method for treatment of osteoarthritis in a subject, which comprises administering to the subject a therapeutically effective amount of a medicament comprising an agent of the formula

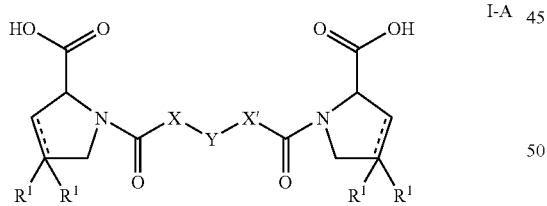

wherein,
$R^1$ is hydrogen or halogen;
X is —$(CH_2)_n$—; —$CH(R^2)(CH_2)_n$—; —$CH_2O(CH_2)_n$—; —$CH_2NH$—; benzyl; —$C(R^2)=CH$—; —$CH_2CH(OH)$—; or thiazol-2,5-diyl;
Y is —S—S—; —$(CH_2)_n$—; —O—; —NH—; —$N(R^2)$—; —CH=CH—; —NHC(O)NH—; —$N(R^2)C(O)N(R^2)$—; —$N[CH_2C_6H_3(OCH_3)_2]$—; $N(CH_2C_6H_5)$—; —$N(CH_2C_6H_5)$—; —$N(CH_2C_6H_5)C(O)N(CH_2C_6H_5)$—; —N(alkoxyalkyl)-; N(cycloalkylmethyl); 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimidoyl, 5-oxo[1,2,4]oxadiazolyl, 2-oxo-[1,2,3,5]oxathiadiazolyl, 5-thioxo[1,2,4]oxadiazolyl and 5-tert-butylsulfanyl-[1,2,4]oxadiazolyl;
X' is —$(CH_2)_n$—; —$(CH_2)_nCH(R^2)$—; —$(CH_2)_nOCH_2$—; —$NHCH_2$—; benzyl, —$CH=C(R^2)$—; —$CH(OH)CH_2$—; or thiazol-2,5-diyl;
$R^2$ is a lower alkyl, lower alkoxy or benzyl; and
n is 0-3,
or a pharmaceutically acceptable salt or mono- or diester thereof,
wherein the agent is capable of inhibiting serum amyloid P component (SAP) ligand binding activity or depleting SAP from the plasma of the subject.

2. A method according to claim 1, wherein the agent inhibits SAP ligand binding activity or depleting SAP from the plasma of the subject by binding to a ligand binding site on SAP.

3. The method of claim 1, wherein,
X is $(CH_2)_n$—; —$CH(R^2)(CH_2)_n$—; —$CH_2$—O—$(CH_2)_n$—; or —$C(R^2)=CH$—;
Y is —$(CH_2)_n$—; —CH=CH—; 1,2-cyclohexyl; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen, wherein the phenylen groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimidoyl, 5-oxo[1,2,4] oxadiazolyl, 2-oxo-[1,2,3,5]oxathiadiazolyl, 5-thioxo[1,2,4] oxadiazolyl and 5-tert-butylsulfanyl-[1,2,4] oxadiazolyl; and
X' is —$(CH_2)_n$—; —$(CH_2)_nCH(R^2)$—; —$(CH_2)_nOCH_2$—; or —$CH=C(R^2)$—.

4. The method of claim 1, wherein,
X is $(CH_2)_n$— or —$CH(R^2)(CH_2)_n$—;
Y is —$(CH_2)_n$—; 1,3-cyclohexyl; 1,4-cyclohexyl; 1,2-naphthyl; 1,4-naphthyl; 1,5-naphthyl; 1,6-naphthyl; biphenylen; or 1,2-phenylen, 1,3-phenylen and 1,4-phenylen; and
X' is $(CH_2)_n$— or —$(CH_2)CH(R^2)$—.

5. The method of claim 1, wherein,
X is —$(CH_2)_n$—;
Y is —$(CH_2)_n$—; and
X' is —$(CH_2)_n$—.

6. A method for treatment of osteoarthritis in a subject, which comprises administering to the subject a therapeutically effective amount of a medicament comprising (R)-1-[6-(R)-2-Carboxy-pyrrolidin-1-yl]-6-oxo-hexanoyl]pyrrolidine-2-carboxylic acid or a pharmaceutically acceptable salt or mono- or diester thereof.

* * * * *

UNITED STATES PATENT AND TRADEMARK OFFICE
CERTIFICATE OF CORRECTION

PATENT NO. : 7,659,299 B2 Page 1 of 1
APPLICATION NO. : 10/559814
DATED : February 9, 2010
INVENTOR(S) : Mark B. Pepys and Philip Nigel Hawkins It is certified that error appears in the above-identified patent and that said Letters Patent is hereby corrected as shown below:

Column 23, line 62, in claim 1 "N(CH$_2$C$_6$H$_5$)–; –N(CH$_2$C$_6$H$_5$)–;" should be changed to "–N(CH$_2$C$_6$H$_5$)–;".

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,659,299 B2 | Page 1 of 1 |
| APPLICATION NO. | : 10/559814 | |
| DATED | : February 9, 2010 | |
| INVENTOR(S) | : Pepys et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 895 days.

Signed and Sealed this

Thirtieth Day of November, 2010

David J. Kappos
*Director of the United States Patent and Trademark Office*